United States Patent
Shaked et al.

(10) Patent No.: US 6,277,411 B1
(45) Date of Patent: Aug. 21, 2001

(54) PHARMACEUTICAL FORMULATION CONTAINING DFMO FOR THE TREATMENT OF CANCER

(75) Inventors: Ze'ev Shaked, Boston, MA (US); James McGinity, Austin, TX (US)

(73) Assignee: ILEX Oncology, Inc., San Antonio, TX (US)

( * ) Notice: Subject to any disclaimer, the term of this patent is extended or adjusted under 35 U.S.C. 154(b) by 0 days.

(21) Appl. No.: 09/210,345

(22) Filed: Dec. 11, 1998

Related U.S. Application Data
(60) Provisional application No. 60/030,266, filed on Nov. 1, 1996.

(51) Int. Cl.$^7$ .............................. A61K 9/14; A61K 35/55; A61K 9/16

(52) U.S. Cl. ........................... 424/489; 424/490; 514/564

(58) Field of Search ................................... 514/561, 564; 424/457, 458, 461, 462, 468, 470, 489, 490, 497

(56) References Cited

U.S. PATENT DOCUMENTS

| | | | |
|---|---|---|---|
| 4,309,442 | 1/1982 | Bey et al. | 424/319 |
| 5,851,537 | 12/1998 | Alberts et al. | 424/400 |

FOREIGN PATENT DOCUMENTS

| | | |
|---|---|---|
| 0255002 | 7/1987 | (EP) . |
| 96/17598 | 6/1996 | (WO) . |

OTHER PUBLICATIONS

Abeloff et al., "Phase I trial and pharmacokinetic studies of α difluoromethylornithine an inhibitor of polyamine biosynthesis," *J. Clin. Oncol.*, 2(2):124–130, 1984.

Abeloff et al., "Phase II trials of α–difluoromethylornithine, an inhibitor of polyamine synthesis in advanced small cell lung cancer and colon cancer," *Cancer Treatment Reports*, 70(7):843–845, 1986.

Alberts et al, "Positive randomized, double blinded, placebo controlled study of topical difluoromethyl ornithine(DFMO) in the chemoprevention of skin cancer," *Proceedings of ASCO*, 15:A342, 1996.

Ansel et al. eds., Pharmaceutical dosage forms and drug delivery systems, 6th Ed., Williams and Wilkins, Baltimore, MD, 1995.

Boyle et al., "Polyamine contents in rectal and buccal mucosae in humans treated with oral difluoromethylornithine," *Cancer Epid. Biomarkers Prevention*, 1(2):131–135, 1992.

(List continued on next page.)

*Primary Examiner*—Thurman K. Page
*Assistant Examiner*—Brian K. Seidleck
(74) *Attorney, Agent, or Firm*—Fulbright & Jaworski

(57) ABSTRACT

Preparations comprising a capsule, tablet or other dosage form containing a core of different types of DFMO are provided. These preparations are capable of providing for the direct and constant delivery of DFMO to the entire GI tract or just the colon and rectum. The DFMO-containing granules include granules specially formulated to achieve rapid DFMO release, and granules formulated to achieve slower DFMO release and/or granules formulated for gastric, enteric or colorectal release. Methods of using the preparations to flood the GI tract with relatively constant levels of DFMO may thus be provided. The ratio of the (+) to the (−)-enantiomeric forms of DFMO in the granules will be controlled so as to enhance the pharmacological profile and reduce toxicity of the preparation relative to racemic DFMO. Preparations and methods for achieving systemic delivery as well as direct colon delivery of DFMO are also described.

7 Claims, 8 Drawing Sheets

OTHER PUBLICATIONS

Carbone et al., "Phase I and pharmacokinetics study of difluoromethylornithine (DFMO) a potential chemopreventive," *Proc. Annul Meet. Am. Assoc. Cancer Res.*, 32:A1209, 1991.

Loprinzi et al., "Inhibition of human skin ornithine decarboxylase activity by oral alpha–difluoromethylornithine," *Cancer Therapy and Control*, 1:75–80, 1989.

Creaven et al., "Evaluation of a α–difluoromethylornithine as a potential chemoprevention agent: tolerance to daily oral administration in humans," *Cancer Epidemiol Biomarkers*, 2:243–247, 1993.

Creaven et al., "Phase I study of difluoromethylornithine DFM as a chemopreventive agent (CPA)," *Proc. Anul. Meet. Am. Soc. Clin. Oncol.*, 11:A395, 1992.

Croghan et al., "Dose–related α–difluoromethylornithine ototoxicity," *Am. J. Clin. Oncol*, 14(4):331–335, 1991.

Crowell et al., "Chronic toxicity studies of the potential cancer preventive 2–(difluoromethyl)–d,1–ornithine," *Fund. Appl. Toxicol.*, 22:341–354, 1994.

Eckhardt et al., "Induction of differentiation in HL60 cells by the reduction of extrachromosomally amplified c–myc," *Proc. Nat'l. Acad. Sci., USA*, 91:6674–6678, 1994.

Garewal et al., "Low dose difluoromethylornithine (DFMO) produces signficiant changes in polyamine content of upper GI mucosa in patients with Barrett's esophagus," *Gastroenterology*, 100(5, Pt 2):A364, 1991.

Garewal, "Chemoprevention of Barrett's esophagus and oral leukiplakia," *The Biology and Prevention of Aerodigestive Tract Cancers*, 129–136, 1992.

Wilding et al., "Enteric coated timed release systems for colonic targeting," *Int. J. Pharmaceutics*, 111:99–102, 1994.

Vandelli et al., "A delayed delivery system for the colonic drug release," Proc. 1st World Mtg., Budapest, 278–279, May 9–11, 1995.

Greenwald et al., "Cancer prevention research trials," *Adv. Cancer Res.*, 61:1–23, 1993.

Griffin et al., "Phase I trial and pharmacokinetic study of intravenous and high dose oral α–difluoromethylornithine," *Proc. ASCO*, 3:34, 1984.

Griffin et al., "Phase I trial and pharmacokinetic study of intravenous and oral α–difluoromethylornithine," *Invest. New Drugs*, 5(2):177–186, 1987.

Van den Mooter et al., "The relation between swelling properties and enzymatic degradation of Azo polymers designed for colon–specific drug delivery," *Pharmaceutical Res.* 11(12):1737–1741, 1994.

Jacoby et al., "Placebo–controlled randomized trial of DFMO as a Chemopreventive agent in patients at high risk for colorectal cancer," *Gastrointestinal Oncol.*, 108(4, Supplement):A485.

Jacoby et al., "Placebo–controlled randomized trial of DFMO as a chemopreventive agent in patients at high risk for colorectal cancer," *J. Invest. Med.*, 43(2):411A, 1995.

Kelloff et al., "Cancer chemopreventive agents: Drug development status II," *J. of Cellular Biochemistry*, Supplement 26, 1996.

Kelloff et al., "Recent results in preclinical and clinical drug development of chemopreventive agents at the National Cancer Institute," *Antimutagenesis and Anticarcinogenesis Mechanisms III*, Plenum Press, New York, 1993 pp. 373–386.

Lieberman et al., eds., Pharmaceutical dosage forms: tablets, Marcel Dekker, Inc., NY, vol. 3, 1990.

Lippman et al., "Cancer chemoprevention," *J. Clin. Oncol.*, 12(4):851–873, 1994.

Liu et al., "Regional chemoprevention of carcinogen–induced tumors in rat colon," *Gastroenterology*, 109(4):1167–1172, 1995.

Van den Mooter et al., "In vivo evaluation of a colon–specific drug delivery system: an absorption study of theopjylline from capsules coated with azo polymers in rats," *Pharmaceutical Res.*, 12(2):244–247, 1995.

Love et al., Randomized phase I chemoprevention dose–seeking study of α–difluoromethylornithine, *J. Natl. Cancer Inst.*, 85(9):732–737, 1993.

Luk, "Clinical and biologic studies of DFMO in the colon," In: *Cancer Chemoprevention*, Wattenberg et al., eds., CRC Press, Boca Raton, FL, 515–530, 1992.

Manchester et al., "Tumour necrosis factor–induced cytotoxicity is accompanied by intracellular mitogenic signals in ME–180 human cervical carcinoma cells," *Biochemical Journal*, 290(1):185–190, Feb. 15, 1993.

McCullough et al, "Regulation of epidermal proliferation in mouse epidermis by combination of difluoromethyl ornithine (DFMO) and methylglyoxal bis(guanylhydrazone)(MGBG)," *J. Investigative Derma.*, 85(6):518–521, 1985.

McGinity, eds., "Aqueous polymeric coatings for pharmaceutical doage forms," Marcel Dekker, Inc., NY, 1989.

Meyskens and Gerner, "Development of difluoromethylornithine as a chemoprevention agent for the management of colon cancer," *J. Cell. Biochem.*, Supp 22:126–131, 1995.

Meyskens et al., "Dose de–escalation chemoprevention trial of α–difuoromethylornithine in patients with colon polyps," *J. Natl. Cancer Inst.*, 86(15):1122–1130, 1994.

Mitchell et al., "Chemoprevention trials and surrogate end point biomarkers in the cervix," *American Cancer Soc. Natl. Conf.*, Apr. 1995.

Nishioka et al., "Polyamines as biomarkers for cervical intraepithelial neoplasia," *J. Cell. Biochem.*, 23:87–95, 1995.

Pendyala et al., "Urinary and erythrocyte polyamines during the evaluation of oral α–difluoromethylornithine in a phase I chemoprevention clinical trial," *Cancer Epidem. Biomarkers, Prevent.*, 2:235–241, 1993.

Rao et al., "Chemoprevention of colon carcinogenesis by dietary administration of piroxicam, α–difluoromethylornithine, 16 α–fluoro–5–androsten–17–one and ellagic acid individually and in combination," *USA Cancer Res.*, 51(17):4528–4534, 1991.

Robinson and Lee, eds., *Controlled Drug Delivery: Fundamentals and Applications*, 2d Ed., Marcel Dekker, Inc. NY, 1987.

Rubinstein et al., "In vitro and in vivo analysis of colon specificity of calcium pectinate formulations," *Eur. J. Pharm. Biopharm.*, 41(5):291–295, 1995.

Scully, "Oral precancer: preventive and medical approaches to management," *Oral Oncol., Eur. J. Cancer.*, 31B(1):16–26, 1995.

Tozer, "Colonic drug delivery," Proceed. Intern. Symp. Control Rel. Bioact. Mater., 17:126–127, Mar. 16, 1990.

Van den Mooter et al., "Characterization of colon–specific azo polymers: a study of the swelling properties and the permeability of isolated polymer films," *Intl. J. Pharmaceutics*, 111:127–136, 1994.

PHARMACEUTICAL FORMULATION CONTAINING DFMO FOR THE TREATMENT OF CANCER

This application claims the benefit of U.S. Provisional App. No. 60/030,266, filed Nov. 1, 1996.

This application is related to PCT No. US97/20424, filed Oct. 31, 1997, designating the United States, the EP Application No. 97946915.2, filed Oct. 31, 1997, the Canadian Application No. 2/241,896, filed Oct. 31, 1997, the Japanese Application No. 10-520855, filed Oct. 31, 1997, and the Mexican Application No. 985376, filed Jul. 1, 1998.

FIELD OF THE INVENTION

The present invention relates to a pharmaceutical formulation and its use for the treatment of cancer. More specifically, the present invention relates to alphadifluoromethylornithine (DFMO) containing oral pharmaceutical formulations having a varied release profile for the treatment of cancer. These formulations may be modified for treating specific cancers.

BACKGROUND OF THE INVENTION

Both in vivo and in vitro, DFMO is an enzyme activated irreversible inhibitor of ornithine decarboxylase (ODC) which is responsible for the conversion of L-ornithine to putrescine, which in turn is converted to longer chain polyamines such as spermidine and spermine. These longer chain polyamines are required for cellular proliferation. Therefore, by inhibiting ODC, DFMO suppresses polyamine formation and consequently cellular proliferation. Aberrant and accelerated cellular proliferation occurs in carcinogenic tissues. Since DFMO is able to suppress polyamine formation, it is able to suppress cellular proliferation and ultimately to ameliorate or prevent cancer. A number of animal studies and/or human clinical trials relate to use of racemic DFMO and specific neoplastic disorders. In addition, a clinical study to determine the pharmacokinetics of racemic DFMO in healthy men has been reported. (Haegele, 1981). Racemic DFMO was reported to have a short elimination half-life, i.e., $t_{1/2}$ is about 3.5 hours, as it undergoes rapid renal elimination. Peak plasma concentrations occur within about 6 hours after oral administration of racemic DFMO containing solutions. Mean total body clearance is about 1.20 mL/min/LcKg, where mean renal clearance is about 0.99 mL/min/LcKg accounting for 83% of drug elimination. The mean apparent volume distribution is about 0.337 L/LcKg, corresponding to 24 L for a 70 LcKg man. The amount of unchanged drug in 24-hour urine samples is about 44% after oral administration and about 80% after L.c. administration.

At a dose of about 3 g/m²V, a steady state level of DFMO, 386–622, $\mu$M may be achieved. A DFMO dose of 2.25 g/m² every six hours has been recommended for Phase II studies in patients previously treated with cytotoxic drugs (Abeloff et al., 1984).

The maximally tolerated dose (MTD) of oral DFMO has also been examined (Abeloff et al., 1984). The MTD of a 4-day DFMO course given orally, by CI, or by pulse IV infusions (Griffin et al., 1987) to patients with advanced solid tumors or lymphomas has also been studied. Some patients receiving twenty-four courses of oral DFMO on a 28-day schedule developed thrombocytopenia (the DLT). Gastrointestinal side effects have also been observed in treated patients (Abeloff et al., 1984). Audiometric abnormalities is a further side effect associated with DFMO treatment (Griffin et al., 1987). No therapeutic responses were noted in these patient populations.

A study by Griffin et al. (1987) compared routes (PO, CI and IV) and schedules (bolus and continuous infusions) of DFMO administration. Nausea and vomiting were the most frequent and severe toxicities noted, but this occurred mainly in patients receiving oral DFMO. Diarrhea was also observed in patients receiving oral DFMO. Mild leukopenia was further observed with all routes of administration. Mild thrombocytopenia also occurred in some patients. No therapeutic responses were reported with any route of drug administration.

The known minimum effective dose (MED) for racemic DFMO in significantly reducing polyamine pools in vivo is about 0.43 g/day. The maximum tolerated dose of these preparations reported is about 12 g/m²/day (oral administration). The reported minimum toxic dose for these racemic preparations of DFMO, in terms of ototoxicity, is about 150 g/m² cumulative dose based upon 0.25–6.0 g/m²/day chronic oral administration. GI toxicity occurs predominantly during P.O. rather than I.V. administration of racemic DFMO preparations. (–)-DFMO has been reported by some to be the enantiomer primarily responsible for ODC inhibition (Danzin, 1987). However, the side effects associated with DFMO have been traced to a particular enantiomeric form.

Tricalcium phosphate (TCP) and aluminum calcium phosphate (AlCAP) capsule formulations have been tested as implants in rats and proposed for the treatment of trypanosomiasis. (Benghuzzi et al., 1988) A layered tablet formulation comprising racemic DFMO and a slow release layer compressed to a rapid release layer has been tested for controlling fertility and gestation in rat and mouse models. (Bey et al., U.S. Pat. No. 4,309,442). Conventional release hard gelatin capsule and tablet formulations comprising racemic DFMO are also known and have been tested in rat, dog and/or mouse models for controlling gestation, treating non-malignant proliferative skin diseases and/or cancer chemoprevention. (Bey et al., U.S. Pat. No. 4,496,588).

A need continues to exist in the medical arts for formulations capable of maintaining high plasma levels of DFMO during therapy in spite of its rapid clearance rate, without the toxic andlor non-pleasant side effects associated with available DFMO therapies.

SUMMARY OF THE INVENTION

It is an object of the present invention to provide an oral solid DFMO-containing pharmaceutical formulation for the treatment or prophylaxis of cancer. The formulations of the invention in some aspects maintain DFMO plasma levels in a patient below the minimum toxic concentration or maximum tolerated concentration and above the minimum effective concentration or minimum therapeutic concentration.

It is yet another object of the invention to provide a method of treating or reducing the risk of cancer by administering to a patient a formulation as described above so as to provide to the gastrointestinal (GI) tract for an extended period of time a therapeutic amount of DFMO.

It is another object of the invention to provide a DFMO-containing dosage form having improved pharmacological activity relative to racemic DFMO. The dosage form will comprise optically pure (–)-DFMO or (+)-DFMO or a defined ratio of (–)-DFMO:(+)-DFMO with reduced side effects or toxicity, enhanced therapeutic efficacy and/or improved pharmacokinetics relative to racemic DFMO.

In one aspect, the invention provides an oral sustained release pharmaceutical formulation for the treatment or prophylaxis of colorectal cancer comprising an oral dosage form. In some embodiments, this dosage form comprises a core and an outer layer surrounding the core, where:
1) the core comprises a rapid release granule and a slow release granule, and each granule comprises a therapeutic amount of (+)-DFMO, (−)-DFMO or a defined ratio of (+)-DFMO:(−)-DFMO or pharmaceutically acceptable salts thereof; and
2) the outer layer comprises a pH-responsive coating for colorectal release of the core.

It is contemplated and within the scope of the invention that a formulation as described above will be useful for the inhibition of cancer or tumor cell proliferation and the amelioration of colorectal cancer.

It is also contemplated and within the scope of the present invention that the pharmaceutical formulation may comprise racemic, optically pure or a defined ratio of the (+):(−) enantiomers of DFMO in combination with other therapeutic compounds for the treatment or prophylaxis of cancer.

It is also contemplated and within the scope of the present invention that the granules which comprise the dosage form core may individually or cooperatively exhibit zero-order, first-order or second-order DFMO release profiles in vivo or in vitro. The rapid release and slow release granules can also act cooperatively to provide a patient being administered the oral sustained release formulation a mean steady state plasma concentration level of (+)-DFMO, (−)-DFMO or a defined ratio of (+)-DFMO:(−)DFMO in the range of about 0.1 $\mu$M to about 1000 $\mu$M.

It is contemplated and within the scope of the invention that the present formulation will provide a therapeutic benefit regardless of the location of the cancer.

In another aspect, the present invention provides an oral sustained release pharmaceutical formulation for the treatment or prophylaxis of colorectal cancer comprising an oral dosage form having a core and an outer layer surrounding the core, where:
1) the core comprises a rapid release granule and a slow release granule, and each granule comprises a therapeutic amount of (+)-DFMO, (−)-DFMO or a defined ratio of (+)-DFMO:(−)-DFMO or pharmaceutically acceptable salts thereof; and
   a) the rapid release granule releases into the colorectal tract a major portion of its DFMO within two hours after dissolution of the outer layer; and
   b) the slow release granule releases into the colorectal tract a major portion of its DFMO within eight hours after dissolution of the outer layer, and
2) the outer layer comprises a pH-responsive coating or bacteria sensitive for colorectal release of the core at or above a pH of about 6.

In another aspect, the present invention provides an oral solid multiple drug release profile pharmaceutical formulation for the treatment or prophylaxis of cancer. In some embodiments, these oral solid multiple drug release profile pharmaceutical formulations comprise an oral dosage form having a core and an outer layer surrounding the core for gastric release of the core, wherein the core comprises DFMO-containing granules having different release characteristics; and the granules comprise (+)-DFMO, (−)-DFMO or a defined ratio of (+)-DFMO:(−)-DFMO, or pharmaceutically acceptable salts thereof.

In another embodiment, the oral solid multiple drug release profile pharmaceutical formulation for the treatment or prophylaxis of cancer comprises: an oral dosage form having a core and an outer layer surrounding the core for gastric release of the core, where the core comprises:

a gastric release granule;
an enteric release granule; and
a colorectal release granule; and
where each granule comprises a therapeutic amount of (+)DFMO, (−)-DFMO or a defined ratio thereof, or pharmaceutically acceptable salts thereof.

It is contemplated and within the scope of the present invention that the dosage form may contain a variety of DFMO containing granules having different release properties for delivery of DFMO throughout the GI tract. The granules maybe present in a range of different weight ratios, may each contain a different amount of DFMO, and may themselves be comprised of other granules. The overall DFMO release profile of this multiple drug release profile pharmaceutical formulation can approximate a zero-ordered controlled release profile.

It is intended that DFMO concentration in plasma will be maintained at or above the minimum effective concentration for a major portion of time during which DFMO-containing granules are present in a patient. The gastric release, enteric release and colorectal release granules can also act cooperatively to provide a patient being administered the oral solid multiple drug release profile pharmaceutical formulation a mean steady state plasma concentration level of (+)-DFMO, (−)-DFMO or a defined ratio of (+)-DFMO:(−)-DFMO in the range of about 0.1 $\mu$M to about 1000 $\mu$M.

Following long-standing patent law convention, the terms "a" and "an" mean "one or more" when used in this specification.

Another aspect of the invention provides an oral sustained release pharmaceutical formulation for the treatment or prophylaxis of colorectal cancer. In some embodiments, the formulation comprises an oral dosage form having a core and an outer layer surrounding the core, where:
1) the core comprises a rapid release granule and a slow release granule, and each granule comprises a therapeutic amount of (+)-DFMO, (−)-DFMO or a defined ratio of (+)-DFMO:(−)-DFMO or pharmaceutically acceptable salts thereof;
2) the rapid release granule further comprises a binder;
3) the slow release granule further comprises a polymer; and
4) the outer layer comprises a pH-responsive coating for colorectal release of the core at or above a pH of about 6.

In yet another aspect, the invention provides an oral solid multiple drug release profile pharmaceutical formulation. In some embodiments, the formulation is employed for the treatment or prophylaxis of cancer. Some of these formulations may be defined as comprising: an oral dosage form having a core and an outer layer surrounding the core for gastric release of the core, where the core comprises:
   a gastric release granule comprising a binder and an excipient;
   an enteric release granule comprising a polymer suitable for enteric drug delivery; and
   a colorectal release granule comprising a polymer which dissolves at a pH greater than or equal to about 6;
wherein each granule comprises a therapeutic amount of (+)DFMO, (−)-DFMO or a defined ratio thereof, or pharmaceutically acceptable salts thereof.

In yet another aspect, the present invention provides an oral sustained release pharmaceutical formulation for the treatment or prophylaxis of colorectal cancer in a patient. In some embodiments, these formulations comprise an oral dosage form having a core and an outer layer surrounding the core where:
the core comprises a rapid release granule and a slow release granule, and each granule comprises a therapeutic amount of (+)-DFMO, (−)-DFMO or a defined ratio of (+)-DFMO:(−)-DFMO or pharmaceutically acceptable salts thereof; and the outer layer comprises a pH-responsive coating for colorectal release of the core;

wherein the slow release and rapid release granules provide a mean steady state plasma concentration level of total DFMO above the minimum effective concentration for a major portion of the time that slow release and/or rapid release granules containing (+)-DFMO, (−)-DFMO or a defined ratio of(+)-DFMO:(−)-DFMO are present in a patient administered the sustained release pharmaceutical formulation.

In another aspect, the invention provides an oral solid multiple drug release profile pharmaceutical formulation for the treatment or prophylaxis of cancer. In some embodiments, the formulation may be defined as comprising: an oral dosage form having a core and an outer layer surrounding the core for gastric release of the core, where the core comprises:

a gastric release granule;

an enteric release granule; and a colorectal release granule;

wherein each granule comprises a therapeutic amount of (+)DFMO, (−)-DFMO or a defined ratio of (+)-DFMO:(−)-DFMO, or pharmaceutically acceptable salts thereof, and the gastric release, enteric release and colorectal release granules cooperatively provide a mean steady state plasma concentration level of total DFMO above the minimum effective concentration for a major portion of the time that gastric release, enteric release and/or colorectal release granules containing (+)-DFMO, (−)-DFMO or a defined ratio of (+)-DFMO:(−)-DFMO are present in a patient administered the multiple drug release profile pharmaceutical formulation.

In yet another aspect, the present invention provides a sustained release or multiple drug release profile pharmaceutical formulation as described above that provides a mean steady state plasma concentration level of total DFMO in the range of about 0.1 $\mu$M to about 1000 $\mu$M, or about 1 $\mu$M to about 100 $\mu$M, or about 1 $\mu$M to about 50 $\mu$M.

The components used in the present invention are available from a variety of commercial sources as follows:"EUDRAGIT™" polymers (Rohm Pharma, Germany), "AQUA-COAT™" and "AQUATERIC™" (F.M.C. Corp., PA), "SURELEASE"™ and "COATERIC™" (Colorcon, Inc., PA), "AQOAT™" (Shin-Etsu Chemical Corp., Japan).

Unless otherwise indicated, all other chemicals were purchased from Aldrich Chemicals (Milwaukee, Wis.) or Sigma Chemical Co. (St. Louis, Mo.). Racemic and enantiomeric forms of DFMO are available from Ilex Oncology.

As used herein, the term "granule" is taken to mean particle, crystal, minitablet, crystal, powder, particulate, or other similar solid forms. The granules used in the invention may display diffusion and/or dissolution controlled release rate profiles according to the components from and processes by which they are made.

As used herein, the term "adsorbent" is intended to mean an agent capable of holding other molecules onto its surface by physical or chemical (chemisorption) means. Such compounds include, by way of example and without limitation, powdered and activated charcoal and the like.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and the like.

As used in the description of the present invention, a granule is defined as, in some embodiments, an agglomerate, a pellet, a tablet, a collection of more than one particle, or a combination of these.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and the like.

As used herein, the term "colorant" is intended to mean a compound used to impart color to liquid and solid (e.g., tablets.and capsules) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red and the like.

As used herein, the term "flavorant" is intended to mean a compound used to impart a pleasant flavor and often odor to a pharmaceutical preparation. In addition to the natural flavorants, many synthetic flavorants are also used. Such compounds include, by way of example and without limitation, anise oil, cinnamon oil, cocoa, menthol, orange oil, peppermint oil and vanillin and the like.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and the like.

As used herein, the term "tablet antiadherents" is intended to mean agents which prevent the sticking of tablet formulation ingredients to punches and dies in a tableting machine during production. Such compounds include, by way of example and without limitation, magnesium stearate and talc and the like.

As used herein, the term "tablet binders" is intended to mean substances used to cause adhesion of powder particles in tablet granulations. Such compounds include, by way of example and without limitation, acacia, alginic acid, carboxymethylcellulose sodium, compressible sugar (e.g., NuTab), ethylcellulose, gelatin, liquid glucose, methylcellulose, povidone and pregelatinized starch and the like.

As used herein, the term "tablet and capsule diluent" is intended to mean inert substances used as fillers to create the desired bulk, flow properties, and compression characteristics in the preparation of tablets and capsules. Such compounds include, by way of example and without limitation, dibasic calcium phosphate, kaolin, lactose, mannitol, microcrystalline cellulose, powdered cellulose, precipitated calcium carbonate, sorbitol, and starch and the like.

As used herein, the term "tablet direct compression excipient" is intended to mean a compound used in direct compression tablet formulations. Such compounds include, by way of example and without limitation, dibasic calcium phosphate (e.g., DITAB) and the like.

As used herein, the term "tablet disintegrant" is intended to mean a compound used in solid dosage forms to promote the disruption of the solid mass into smaller particles which are more readily dispersed or dissolved. Such compounds include, by way of example and without limitation, alginic acid, carboxymethylcellulose calcium, microcrystalline cellulose (e.g., AVICEL), polacrilin potassium (e.g., AMBERLITE), sodium alginate, sodium starch glycollate, and starch and the like.

As used herein, the term "tablet glidant" is intended to mean agents used in tablet and capsule formulations to reduce friction during tablet compression. Such compounds include, by way of example and without limitation, colloidal silica, cornstarch, and talc and the like.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and the like.

As used herein, the term "tablet/capsule opaquant" is intended to mean a compound used to render a capsule or a tablet coating opaque. May be used alone or in combination with a colorant. Such compounds include, by way of example and without limitation, titanium dioxide and the like.

As used herein, the term "tablet polishing agent" is intended to mean a compound used to impart an attractive sheen to coated tablets. Such compounds include, by way of example and without limitation, carnauba wax, and white wax and the like.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The term "unit dosage form" is used herein to mean a single or multiple dose form containing a quantity of the therapeutic compound containing formulation, said quantity being such that one or more predetermined units are normally required for a single therapeutic administration. In the case of multiple dose forms, such as scored tablets, said predetermined unit will be one fraction, such as ½, of a scored tablet.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, the term DFMO is intended to mean alpha-difluoromethylornithine in its pharmaceutically acceptable salt and/or isomeric forms. (+)-DFMO is intended to mean a substantially optically pure preparation of alpha-difluoromethylornithine having the (D)-configuration around the alpha-carbon of the molecule. (−)-DFMO is intended to mean a substantially optically pure preparation of alpha-difluoromethylornithine having the (L)-configuration around the alpha carbon. By "a defined ratio of (+)-DFMO:(−)-DFMO" is meant a ratio of the individual DFMO optical isomers in the range of about 5–95% wt:95–5% wt., respectively. By "substantially optically pure preparation" is meant a preparation of a first enantiomer which contains about 5% wt. or less of the opposite enantiomer. By "total DFMO" is meant the total amount of DFMO present, i.e., the sum total of its enantiomers, in plasma, for example.

Other features, advantages and embodiments of the invention will be apparent to those skilled in the art from the following description, accompanying data and appended claims.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

The subcoat of Opadry® II may comprise a 2% to 3% weight gain of HPMC. The acrylic polymeric coating may then be applied by spraying the polymer over the subcoat. The retardant polymer coat in some embodiments may be expressed as an amount that comprises about an 8% to an about 18% net weight gain. By way of example, these polymers may comprise EUDRAGIT™ L30D-55 or EUDRAGIT™ 4110D.

The release profiles in an acidic media reflect poor adhesion of the anionic polymers to the wax pellets containing DFMO. The rapid release of the drug in the absence of the subcoat was evident from both pellet formulations in the acidic medium as demonstrated in FIG. 19.

Figure 20:
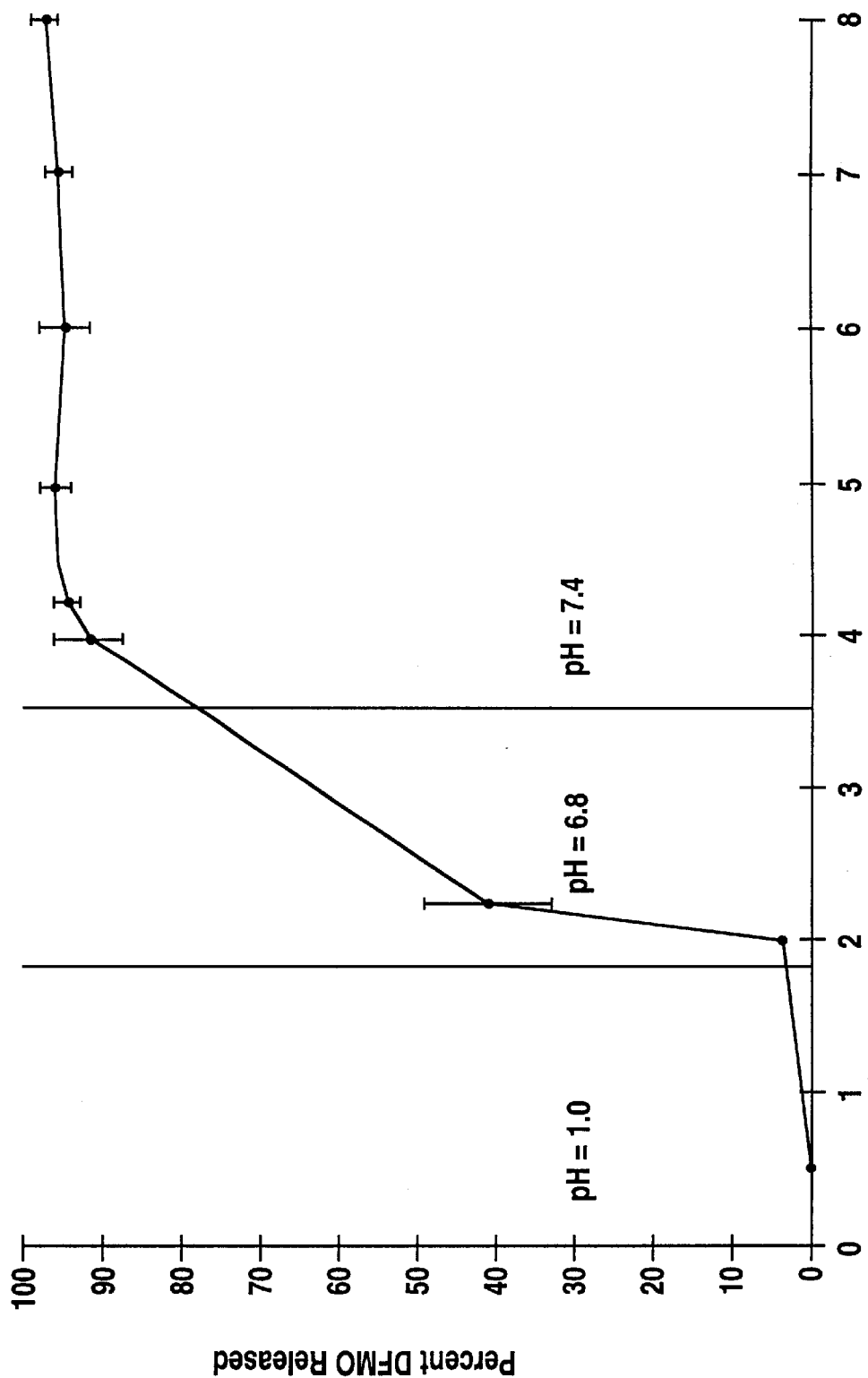

FIG. 20. Demonstrates profile of a slow release matrix pellet formulation that was first coated with an ethyl cellulose dispersion (AQUACOAT®) containing HPMC, and then coated with EUDRAGIT™ 4110D.

DETAILED DESCRIPTION OF THE PREFERRED EMBODIMENTS

The present invention provides a variety of combined varied-release pharmaceutical formulations that include DFMO, and provide for its delivery in preparations designed to be capable of sustaining a desired release profile and/or plasma concentration tailored to the pathology or condition being treated. The particular preparations described below are examples of some of these formulations and variations thereof in view of same are intended as within the scope of the invention.

Dosage Form Outer Layer

The dosage form outer layer (7) which surrounds the dosage form core comprising granules (5) and (6) will generally be insoluble in gastric juices and will release the core in a pH-responsive fashion. Advantageously, the outer layer will release the core upon exposure to a pH of about 6 or higher and will generally have released the dosage form core contents directly into the colorectal tract of a patient. By targeting the colorectal tract for DFMO delivery, the present formulation will find use in the treatment and/or prevention of colorectal cancer or other polyamine dependent colorectal disorders such as premalignant polyps.

By "pH-responsive" is meant a pH-dependent fashion, i.e. the outer layer, when exposed to a certain pH, will deliver the dosage form core to the colorectal tract. Advantageously, the outer layer will be comprised of a pH-responsive polymer that will dissolve when exposed to a pH greater than or equal to about 6; although, the pH-responsive polymer may dissolve at a pH greater than or equal to about 5.

The outer layer will comprise, by way of example and without limitation, a polymeric compound such as EUDRAGIT™ RS and EUDRAGIT™ RL. The EUDRAGIT™ products form latex dispersions of about 30D by weight. EUDRAGIT™ RS 30D is designed for slow release since it is not very water permeable as a coating and EUDRAGIT™ RS 30D is designed for rapid release since it is relatively water permeable as a coating. These two polymers are generally used in combination. As contemplated herein, the permissible ratios of EUDRAGIT™ RS 30D/ EUDRAGIT™ RL 30D is about 10:0 to about 8:2. Ethylcellulose or S100 or other equivalent polymers designed for enteric or colorectal release can also be used in place of the EUDRAGIT™ RS/EUDRAGIT™ RL combination above. The outer layer can also comprise dyes, dissolution aids, colorants and pigments. Such components for the outer layer are available from Colorcon (Delaware) or Crompton & Knowles (New Jersey).

Rapid Release Granule in the Dosage Form Core

Figure 8:
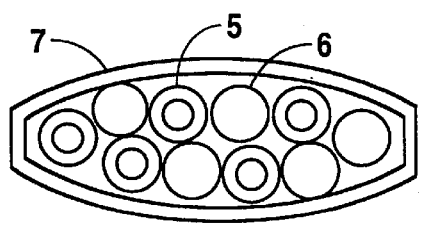
FIG. 8. A first embodiment of a dosage form for the sustained release formulation. 5=coated pellet; 6=rapid release pellet; 7=retardant coating or immediate release coating.

With particular attention to FIG. 8, rapid release granules (6) will comprise part of the dosage form core which is surrounded in its entirety by the outer layer (7). The rapid release granule will generally not be soluble in gastric juices and need not be soluble in enteric or colorectal fluids. It may release DFMO in either a pH-dependent or pH-independent fashion and/or a zero-order, first-order or second-order fashion. The rapid release granule will generally be a dissolution controlled formulation. The rapid release granule may provide a patient with a loading dose of DFMO to quickly establish in the patient a target DFMO plasma concentration level which is generally above the minimum effective concentration (MEC) of DFMO. Alternatively, the rapid release granule will permit the direct rather than systemic exposure of colorectal mucosa to DFMO.

The rapid release granule containing DFMO will advantageously have released into the colorectal tract a major portion of its DFMO within two hours after dissolution of the dosage form outer layer. Although intended for colorectal release, it is possible this granule will release some of its DFMO upstream in the GI tract if the dosage form outer layer has dissolved prematurely.

The rapid release granule will comprise DFMO and other compounds such as starch, talc, sugar, magnesium stearate, microcrystalline cellulose (MCC), lactose and pregelatinized starch. The rapid release granule can also comprise dissolution aids, stability modifiers, adsorption promoters, bioadhesive polymers and density modifiers.

Figure 9:
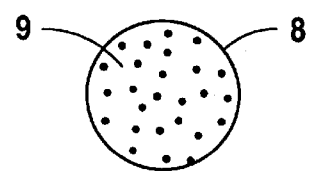
FIG. 9. Cross-sectional view of a matrix rapid release granule of the invention. 8=spherical pellet; 9=drug in pellet core.
Figure 10:
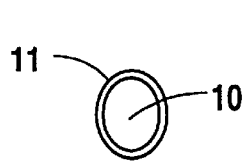
FIG. 10. Cross-sectional view of a coated rapid release granule of the invention. 10=drug in core; 11=coating.
Figure 11:
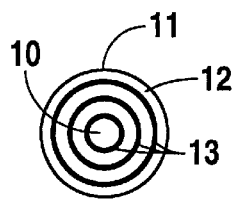
FIG. 11. Cross-sectional view of a multi-layered rapid release granule of the invention. 10=drug in core; 11=multi coated pellet; 12=immediate release coating that may contain drugs; 13=coatings that dissolve or disintegrate as a function of pH or microbial interaction.

The rapid release granule may be, by way of example and without limitation, a quickly dissolving polymeric matrix (9) having DFMO (8) dispersed therein (FIG. 9), a DFMO core (10) surrounded by a rapidly dissolving coating (11) (FIG. 10), a multi-layered granule having a non-pareil core (12) surrounded by alternating layers of DFMO (13) and a binder (14) (FIG. 11) or a spheronized bead comprising DFMO, binder and excipient integrally mixed therein.

Methods for the preparation of rapid release granules are well known in the art and depend upon whether the release is to be pH-dependent or pH-independent; or zero-order, first-order or second-order. One method for the preparation of these granules is detailed in Example 2.

By "binder" is meant compounds such as hydroxypropylcellulose (HPC), hydroxypropylmethylcellulose (HPMC), methylcellulose and the like. By "excipient" is meant an inactive adjuvant ingredient used in processing pharmaceutical solid dosage forms that aids in the manufacturing and processing or has a functional purpose after administration to a patient, e.g. disintegration aid. Binders include, by way of example and without limitation, compounds such as microcrystalline cellulose (MCC), carbohydrates, polysaccharides, pregelatinized starches, calcium phosphate, calcium sulfate, starches and polymeric excipients.

Slow Release Granule in the Dosage Form Core

With particular attention to FIG. 8, slow release granules (5) will comprise part of the dosage form core which is surrounded in its entirety by the outer layer (7). The slow release granule will generally not be soluble in gastric juices and may release its DFMO in either a pH-dependent or pH-independent fashion. The slow release granule can maintain DFMO plasma concentration levels at or about the concentrations achieved by the rapid release granule. By virtue of its release profile, the slow release granule will provide the colorectal mucosa with both direct and systemic exposure to DFMO.

The slow release granule containing DFMO will generally release a major portion of its DFMO into the large intestine (colon) and the rectum a major portion of its DFMO within eight hours after dissolution of the dosage form outer layer. Although intended for colorectal release, it is possible this granule will release some of its DFMO prior to entering the colon if the dosage form outer layer has dissolved prematurely.

The slow release granule will comprise DFMO and a polymer. Such polymers include EUDRAGIT™ S100, EUDRAGIT™ RS30D/EUDRAGIT™ RL 30D, hydrophilic colloidal celluloses, aqueous dispersions of cellulose, such as AQUA-COAT™ and SURELEASE, polysaccharides, such as sodium alginate, xanthan gum, proteins, gelatins, chitosan, clays, such asmerilonite, poly (ethylene oxide), bioadhesives, acrylic vinyl resins, such as CARBOPOL, polyacrylic acid resins, such as POLYCARBOPHYL, waxes, hydrogenated castor oil and high molecular weight vegetable oils.

The slow release granule may be, by way of example and without limitation, a slow dissolving/releasing polymeric matrix having DFMO dispersed therein or a DFMO-containing core surrounded by a slow releasing polymeric layer.

Methods for the preparation of slow release granules are well known in the art and depend upon whether the release is to be pH-dependent or pH-independent; diffusion or dissolution controlled; or zero-order, first-order or second-order. One method for the preparation of these granules is detailed in Example 3.

Dosage Formulation

FIG. 8 depicts one embodiment of the sustained release formulation of the present invention. In this caplet dosage form, the rapid release granules (6) together with the slow releases granules (5) are surrounded by a pH responsive outer layer (7). This embodiment comprises an outer layer (7), a rapid release granule (6) and a slow release granule (5). This dosage form may be a capsule, gelcap or caplet. With particular attention to FIG. 12, the present dosage form may also be a tablet where a core (15), comprising a slow releasing polymeric matrix having DFMO dispersed therein is surrounded by a layer (16), comprising DFMO integrally mixed with a binder and an excipient, which is then surrounded by a pH responsive outer layer (7). Referring now to FIG. 13, the dosage form can also be a tablet where the core (20) comprises DFMO (17) and slow release granules (5) dispersed therein. The slow release granules (5) comprise a pH responsive coating (18) surrounding a DFMO core (19). The tablet core (20) is surrounded by a pH responsive coating (7).

Figure 2:
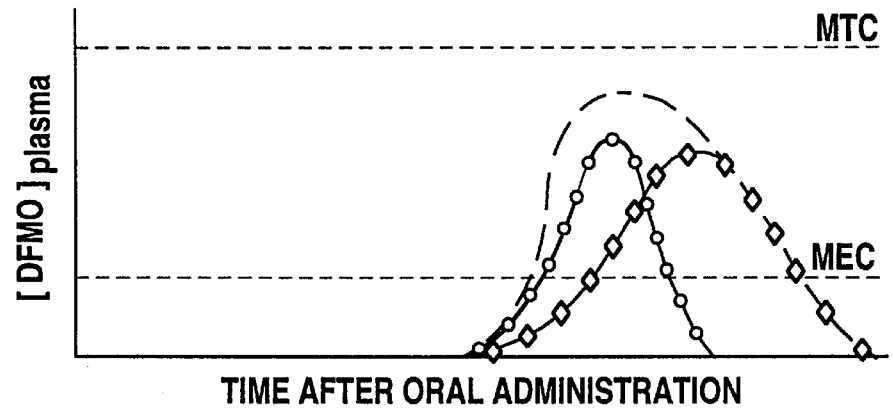
FIG. 2. Representations of the approximate DFMO release profiles for three embodiments of the sustained release formulation. The rapid colorectal release profile is demonstrated as open circles (-○-○-○-). The slow colonic release profile is demonstrated as open diamonds (-◇-◇-◇-). The rapid release pellets in this profile (-◇-◇-◇-) were first coated with EUDRAGIT™ 4110D RS 30D and RL 30D and then coated with EUDRAGIT™ 4110D. The composite total formulation provides a DFMO drug release profile that is presented in a graph as a dashed line (- - -). Modified ratios of these two types of coated granules may be created to provide the desired drug delivery profile.

FIG. 2 shows the expected plasma DFMO concentration profile expected when one embodiment of the sustained release formulation of the present invention is used. MTC indicates the minimum toxic concentration as determined by plasma concentration of DFMO. MEC indicates the minimum effective concentration. It is intended that the mean plasma drug concentration level, as indicated by the curved dashed line, will not drop below the MEC for a major portion of the time in which DFMO-containing granules remain in a patient. It is also intended that the two granules will act cooperatively to yield an approximate overall zero-order controlled release profile for the formulation as a whole.

The DFMO plasma concentration profile in a patient is the sum total of the release profiles of each given granule in a dosage form. Thus, various combinations of granules having different release profiles can act cooperatively to generate a DFMO plasma concentration profile as shown in FIG. 2.25.

FIG. 2 shows how a first rapid colorectal releasing granule and a second slow colorectal releasing granule can act cooperatively to yield the desired overall DFMO plasma concentration profile for the sustained release formulation of the invention. DFMO plasma concentration is maintained between the MTC and MEC for a major portion of the time in which DFMO-containing granules are present in a patient. As per the area under the curve, the total amount of DFMO released by the rapid release granules can be less than that released by the slow release granules.

Figure 4:
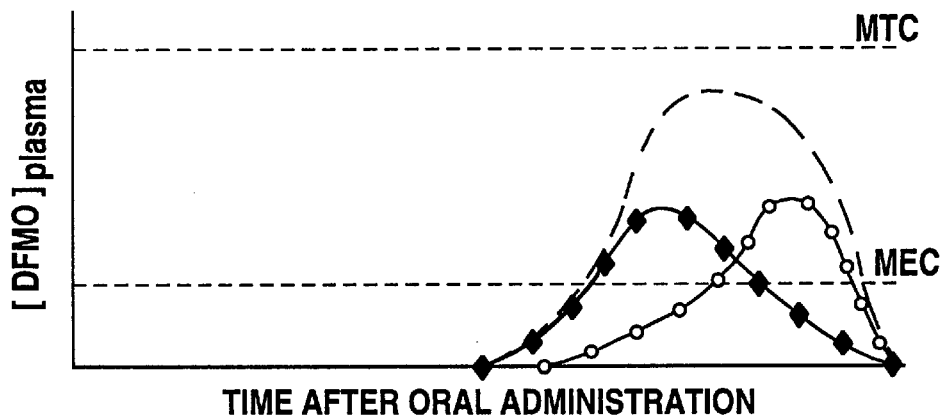
FIG. 4. Proposed in vivo plasma release of DFMO for matrix pellets coated with EUDRAGIT™ 4110D is demonstrated on the graph as filled diamonds (-◆-◆-◆-). The rapid release granules of DFMO were first coated with AQUACOAT® containing HPMC and then coated with EUDRAGIT™ 4110D (open circles, -○-○-○-). The combination of these two pellets is also shown as the dashed line (- - -).

FIG. 4 shows how a first slow colorectal releasing granule and a second rapid colorectal releasing granule can act cooperatively to yield the desired DFMO plasma concentration profile for the sustained released formulation of the invention.

It should be understood that specific release profiles for each granule will vary. It is contemplated and within the scope of the invention that various release profile shapes may be attained by each granule without departing from the spirit and scope of the invention.

It should also be understood that the MEC will vary according to the indication being treated, patient response, the DFMO form being used, dosing regimen and a host of other reasons. It is generally intended when referring to the MEC that the total amount of DFMO present in plasma is being contemplated. When administered acutely, the MEC for DFMO will generally be higher than when it is administered chronically. When administered for preventing or reducing the risk of cancer, the MEC for DFMO will generally be lower than when it is administered for treating or controlling the growth of cancer.

The MEC based upon mean steady state plasma concentration for DFMO will generally fall in the range of about 0.1 $\mu$M to about 1000 $\mu$M and preferably in the range of about 1 $\mu$M to about 100 $\mu$M and more preferably in the range of about 1 $\mu$M to about 50 $\mu$M. It should be understood that the maximum concentration level (Cmax) of DFMO will exceed the MEC but will generally be less than the MTC.

Thus according to one embodiment of the sustained release formulation of the invention, the slow release and rapid release granules will act cooperatively to provide a mean steady plasma concentration level for DFMO in the range of about 0.1 $\mu$M to about 1000 $\mu$M and preferably in the range of about 1 $\mu$M to about 100 $\mu$M and more preferably in the range of about 1 $\mu$M to about 50 $\mu$M.

The rapid and slow release granules of the invention may each be present in a wide range of amounts according to the formulation DFMO release profile desired. By way of example and without limitation, if both granules had the same amount of DFMO, it may be desirable to include the granules in the following ratio about 1:5 parts by weight (rapid:slow release granule) if predominantly direct flooding of the colorectal tract by DFMO were desirable and if greater emphasis on sustaining a long DFMO release profile were desired. Conversely, the ratio of about 5:1 parts by weight (rapid:slow release granule) would give predominantly systemic exposure of the colorectal tract to DFMO and would emphasize the rapid attainment of a maintenance plasma DFMO concentration. The exact ratio chosen will depend upon individual patient response to DFMO therapy, the extent of colorectal cancer progression, the optical form of the DFMO administered, the actual dosage of DFMO in each granule or the desired dosing regimen.

Generally, each granule will be present in the range of about 1.0 to about 9.0 parts by weight using about 10 parts by weight as the basis for the total number of parts which the dosage form may contain, i.e. the granules will generally be present in the ratio of about 1.0—about 9.0:about 1.0—about 9.0 parts by weight (rapid:slow release granule). Rather than to vary the relative amounts of rapid release and slow release it may be desirable to vary the amount of DFMO is each granule.

The dosage form of the present invention can be a tablet, caplet, gelcap or capsule, e.g. hard gelatin or soft gelatin capsule. When the sustained release formulation of the invention takes the form of a gelcap, caplet or tablet, the granules may be held together by and coated with a pH responsive layer that dissolves in colorectal fluids thereby releasing the granules in the colorectal tract and directly flooding it with DFMO.

When the dosage form is a capsule containing rapid and slow release particle, it may generally be prepared as follows. A capsule outer layer comprised of an upper half and a lower half is preformed of a material which is pH responsive and soluble in colorectal fluids. The lower half is filled with core contents such as rapid and slow release granules and then capped (sealed) with the upper half to form a capsule shaped dosage form. The relative sizes of the halves as well as the final size of the capsule outer layer generally depend upon the size and weight of the capsule core.

As used herein, the term "therapeutic compound" is taken to mean a compound having the desired beneficial pharmacologic and therapeutic effects in mammals. Advantageously, the therapeutic compound is also cytoxic or cytostatic and indicated for the treatment or prophylaxis of cancer.

The therapeutic compounds contemplated within the scope of the invention may be in their free acid, free base, or pharmaceutically acceptable salt forms. They may be derivatives or prodrugs of a given compound.

Loading of the therapeutic compounds into a pharmaceutical formulation may be accomplished following well known techniques such as those described [in] Remington's Pharmaceutical Sciences, 17th ed., Mack Publishing Company, Easton, Pa., 1985, the disclosure of which is hereby incorporated by reference.

Therapeutic compound loading into the formulation may need to be varied according to the pharmacological activity of the compound, the indication being treated, the targeted dosing regimen, the projected method of administration, the integrity or stability of the final formulation or other such reasons.

Multiple Drug Release Profile Formulation

Figure 7:
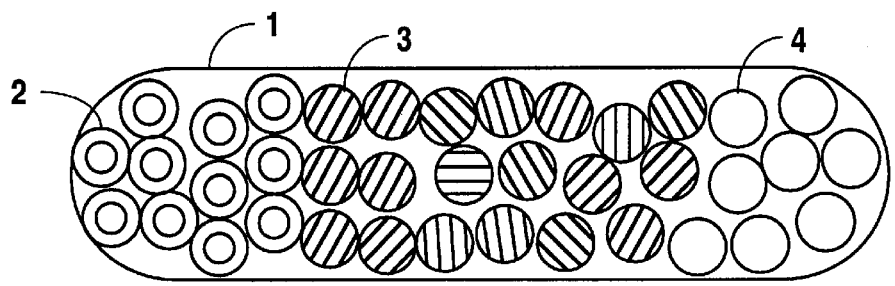
FIG. 7. A first embodiment of a dosage form for the multiple drug release profile formulation. 1=hard gelatin capsule or caplet shaped tablet; 2=coated pellet; 3=matrix slow release pellet; 4=rapid release pellet.

FIG. 7 shows a capsule or tablet dosage form (1) for the multiple drug release profile formulation of the invention which comprises a gastric release granule (4), an enteric release granule (3) and a colorectal coated pellet (2). The multiple drug release profile formulation will deliver DFMO throughout the entire gastrointestinal (GI) tract. This type of delivery will permit its use in treating, preventing and/or controlling the growth of a wide variety of cancers and tumors such as, by way of example and without limitation, neuroblastoma, colon carcinoma, leukemia, hepatoma, mammary sarcoma, small cell lung cancer, pancreatic tumor, Lewis lung carcinoma, B16 murine melanoma, M3 murine adenocarcinoma, bladder carcinoma, endocervical carcinoma, epithelial cancer, chemically induced cancer, metastatic colorectal cancer, refractory childhood leukemia, cervical intraepithelial neoplasia grade 3 (CIN III), hematological malignancies, acute and chronic myeloid leukemia, recurrent glioma and glioblastoma, solid tumor, lymphoma, mammary carcinoma, premalignant polyps and Barrett's esophagus.

Dosage Form Outer Layer

The dosage form outer layer which surrounds the dosage form core will be soluble in gastric juices and may release the core in either a pH-dependent or pH-independent fashion.

The dosage form outer layer will generally have released the dosage form core contents within two hours of administration of the dosage form to a patient.

The dosage form outer layer can be a film coating comprising a polymer such as, by way of example and without limitation, hydroxypropylcellulose (HPC), ethylcellulose (EC), hydroxypropylmethylcellulose (HMPC), hydroxyethylcellulose (HEC), sodium carboxymethylcellulose(CMC), poly(vinyl pyrrolidone) (PVP), poly(ethylene glycol) (PEG), dimethylaminoethyl methacrylate-methacrylic acid ester copolymer, or ethylacrylate-methylmethacrylate copolymer (EA-MMA). The outer layer can also comprise dyes, dissolution aids, colorants, pigments, antiadhesives, surfactants, antifoaming agents and stabilizers.

Gastric Release Granule in Dosage Form Core

In one aspect, the invention provides a dosage form core that comprises a gastric release granule (4) and will be surrounded in its entirety by the dosage form outer layer (1) (FIG. 7). The gastric release granule need not be soluble in gastric juices and may release DFMO in either a pH-dependent or pH-independent fashion.

The gastric release granule containing DFMO will generally have released into the stomach a major portion of its DFMO within two hours of administration of the dosage form to a patient. Although intended for gastric release, it is possible this granule will release some of its DFMO farther down the GI tract.

The gastric release granule will comprise DFMO and a binder such as, by way of example and without limitation, hydroxypropylmethylcellulose (HPMC), ethylcellulose (EC), hydroxyethylcellulose (HEC), sodium carboxymethylcellulose (CMC), poly(vinyl pyrrolidone) (PVP), poly (ethylene glycol) (PEG), dimethylaminoethyl methacrylate-methacrylic acid ester copolymer, or ethylacrylate-methylmethacrylate copolymer (GA-MMA) along with a filler excipient. The gastric release granule can also comprise dissolution aids, stability modifiers, adsorption promoters, bioadhesive polymers, and plasticizers.

Methods for the preparation of gastric release granules are well known in the art and depend upon whether the release is to be pH dependent or pH-independent; or zero order, first-order or second-order. One method for the preparation of the gastric release granule is detailed in Example 5.

Enteric Release Granule in the Dosage Form Core

In one aspect of the invention, the dosage form core will comprise an enteric release granule (3) and will be surrounded in its entirety by the dosage form outer layer (1) (FIG. 7). The enteric release granule will generally not be soluble in gastric juices and may release its DFMO in either a pH-dependent or pH-independent fashion.

The enteric release granule containing DFMO will generally have released into the small intestine a major portion of its DFMO within about six to eight hours of administration of the dosage form to a patient. Although intended for intestinal release, it is possible his granule will release some of its DFMO either prior to entering the small intestine or farther down the GI tract.

The enteric release granule will comprise DFMO and a polymer suitable for enteric drug delivery such as, by way of example and without limitation, cellulose acetate phthalate (CAP), cellulose acetate trimelletate (CAT), poly (vinyl acetate) phthalate (PVAP), hydroxypropylmethylcellulose phthalate (HP), poly(methacrylate ethylacrylate) (1:1) copolymer (MA-EA), poly(methacrylate methylmethacrylate) (1:1) copolymer (MA MMA), poly (methacrylate methylmethacrylate) (1:2) copolymer, EUDRAGIT™ L 30D (MA-EA, 1:1), EUDRAGIT™ 100 55 (MA-EA, 3:1), hydroxypropylmethylcellulose acetate succinate (HPMCAS), SURETERIC (PVAP), AQUA-TERIC™ (CAP), shellac or AQOAT™ (HPMCAS). The enteric release granule can also comprise dissolution aids, stability modifiers, adsorption promoters, bioadhesive polymers and plasticizers.

Methods for the preparation of enteric release granules are well known in the art and depend upon whether the release is to be pH-dependent or pH-independent; diffusion or dissolution controlled; zero-order, first-order or second-order, or rapid, slow or sustained release. One method for the preparation of these granules is detailed in Example 6.

Colorectal Release Granule in the Dosage Form Core

In one aspect of the invention, the dosage form core will comprise a colorectal release granule (2) and will be surrounded in its entirety by the dosage form outer layer (1) (FIG. 7). The colorectal release granule need will generally not be soluble in gastric juices and may release its DFMO in either a pH-dependent or pH-independent fashion.

The colorectal release granule containing DFMO will generally have released into the large intestine (colon) and the rectum a major portion of its DFMO within about ten to sixteen hours of administration of the dosage form to a patient. Although intended for colorectal release, it is possible this granule will release some of its DFMO prior to entering the colon.

The colorectal release granule will comprise DFMO and many of the same or similar polymers employed in the enteric granule the main difference being that a thicker coating of the polymer and that a polymer which dissolves at a pH greater than or equal to about 6 will be used. Targeted colonic delivery systems are known and employ materials such as hydroxypropylcellulose, microcrystalline cellulose (MCE, AVICEL™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA:MMA:MA synthesized in the presence of N,N'-bis (methacryloyloxyethyloxycarbonylamino)-azobenzene, azopolymers, enteric coated timed release system (TIME CLOCK® from Pharmaceutical Profiles, Ltd., UK) and calcium pectinate and the osmotic minipump system (ALZA corp.). The colorectal release granule can also comprise dissolution aids, stability modifiers, adsorption promoters, bioadhesive polymers and plasticizers.

Methods for the preparation of colorectal release granules are well known in the art and depend upon whether the release is to be pH-dependent or pH-independent; diffusion or dissolution controlled; zero-order, first-order or second-order; or rapid, slow or sustained release. One method for the preparation of these polymers is detailed in Example 7.

Sustained Release Granule

This granule is optionally present in the formulations of the invention. When present, the sustained release granules will comprise part of the dosage form core which is surrounded in its entirety by the dosage form outer layer. The sustained release granule may or may not be soluble in gastric or intestinal fluids and may release its DFMO in either a pH-dependent or pH-independent fashion.

The sustained release granule containing DFMO can release DFMO throughout the entire digestive tract or in targeted portions of the GI tract.

The sustained release granule will comprise DFMO and, by way of example and without limitation, shellac, zein, ethylcellulose (EC), cellulose esters (such as acetate), silicone elastomers, acrylate esters or fats and waxes (such as beeswax, carnauba wax), hydrogenated castor oil and vegetable oils, cetyl alcohol, cetylstearyl alcohol, SURELEASE™ (EC), AQUA-COAT™ ™ (EC), EUDRAGIT™ NE 30D™ (EA-MMA), EUDRAGIT™ RL 30D™ (poly[ethylacrylate-methylmethacylate]triethylammonioethyl methacrylate chloride, EA-MMA-TEAE, 1:2:0.2) or EUDRAGIT™ RS 30D™ (EA-MMA-TEAE, 1:2:0.1). The sustained release granule can also comprise dissolution aids, stability modifiers, adsorption promoters, bioadhesive polymers and plasticizers.

Methods for the preparation of sustained release granules for release of therapeutic compound throughout the digestive tract are well known in the art and depend upon whether the release is to be pH-dependent or pH-independent; diffusion or dissolution controlled; or zero-order, first order or second-order release. One method for the preparation of these granules is detailed in Example 8.

Multiple Drug Release Profile Capsule Dosage Form

FIG. 7 depicts one embodiment of this dosage form. Within the capsule core are enteric (3), gastric (4), and colorectal (2) release granules. The outer layer (1) is shown as having a capsule shape but may possess any desired shape.

Figure 1:
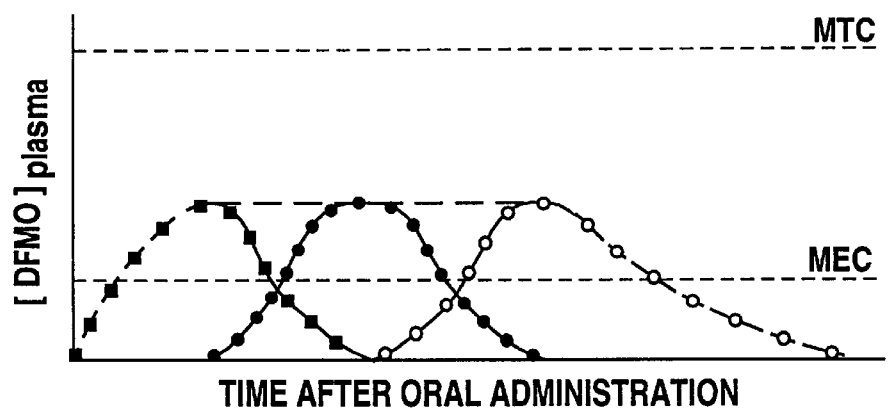
FIG. 1. Representations of the approximate DFMO release profiles for various embodiments of the multiple drug release profile formulation (compound preparation (a rapid release uncoated pellet of DFMO, on enteric coated rapid release pellet and colonic coated, rapid release pellets in combination) in a solid dosage form is represented. The plasma time release profile of DFMO after oral administration of the product containing the above compound is shown. The plasma time release profile of DFMO after oral administration of the rapid gastric release preparation in a solid dosage form is demonstrated in FIG. 1. The rapid gastric release preparation is presented as solid squares (-■-■-■-). The plasma release profile of DFMO after oral administration of the enteric coated rapid enteric release preparation in a solid dosage form is presented as solid circles (-●-●-●-). The colonic coated rapid release preparation in a solid dosage form is presented as open circles (-○-○-○-). The "total" line is presented as a dashed line (- - -), and represents DFMO drug release in a composite tablet or capsule that includes the coated and uncoated particles in combination. The combination of these various pellets may be changed to provide the desired drug delivery to target sites in the GI tract by modifying the amount of drug to be delivered with the desired coating to achieve the gastric, enteric or colorectal release of the agent.

FIG. 1 shows the expected plasma DFMO concentration profile expected when one embodiment of the multiple drug release profile formulation of the present invention is used. It is intended that the mean plasma drug concentration level will be maintained at or above the MEC for a major portion of the time in which DFMO-containing granules remain in the GI tract. It is also intended that the granules will act cooperatively to yield overall an approximately zero-order controlled release profile. Three different types of rapid gastric, enteric and colorectal release granules can combine to yield the desired overall DFMO plasma concentration profile.

Figure 3:
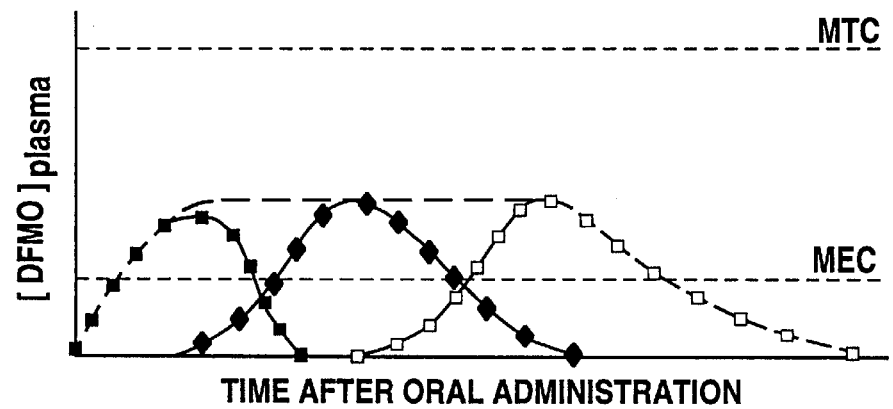
FIG. 3. The slow enteric release DFMO drug release labelled profile comprises a slow release matrix pellet formulation as described in Example 15, table 31. The slow enteric release coated preparation provides a drug release profile as noted in the filled diamonds (-◆-◆-◆-). The rapid gastric release preparation is expected to provide a DFMO drug release profile as noted in the solid squares (-■-■-■-). The slow colorectal release preparation will provide an expected DFMO release profile as presented in the open squares (-□-□-□-). The slow release matrix pellets were first coated with Opadry® II and then EUDRAGIT™ 4110D. The in vitro dissolution profile of these uncoated slow release matrix pellets appear at FIG. 18.
Figure 5:
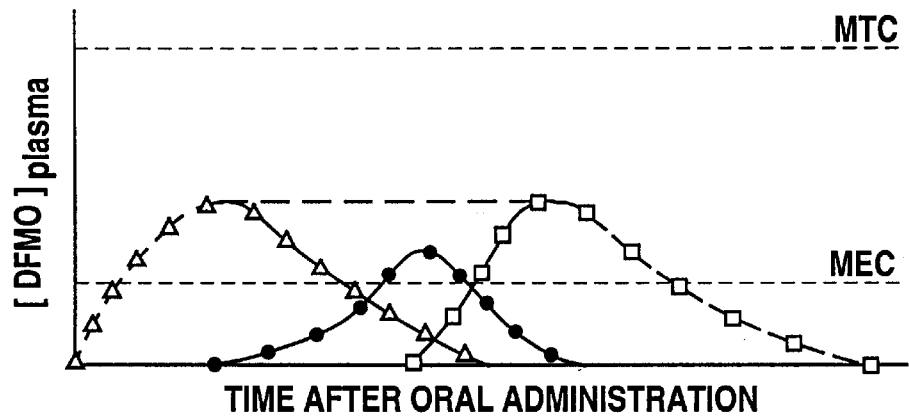
FIG. 5. Proposed in vivo plasma release profile of DFMO. The proposed enteric coated rapid gastric release pellet is presented as filled circles (-●-●-●-). The proposed slow release uncoated maxtix pellets provide a release profile presented as open triangles (-Δ-Δ-Δ-). The proposed colorectal coated slow release matrix pellets are presented as open squares (-□-□-□-). The proposed DFMO drug release profile is presented as a dashed line (- - -).
Figure 6:
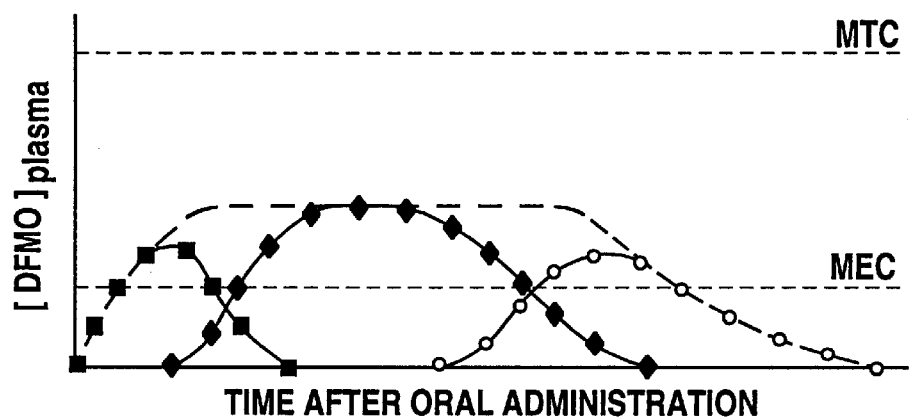
FIG. 6. Proposed in vivo plasma release profile of DFMO. The proposed rapid gastric release coated pellet profile is presented as filled squares (-■-■-■-). The enteric coated slow release matrix pellets are presented as solid diamonds (-♦-♦-♦-). The colorectal coated rapid release pellets are presented as open circles (-○-○-○-).

Various combinations of rapid and slow gastric, enteric and colorectal release granules can act cooperatively to yield the desired overall DFMO plasma concentration profile. FIG. 3 shows the combination of a rapid gastric release granule, a slow enteric release granule and a slow colorectal release granule to yield the desired DFMO plasma concentration profile. FIG. 5 shows the combination of a slow gastric release granule, a rapid enteric release granule and a slow colorectal release granule to yield the desired overall DFMO plasma concentration profile. FIG. 6 shows the combination of a rapid gastric release granule, a slow enteric release granule and a rapid colorectal release granule to yield the desired overall DFMO plasma concentration profile.

Though specific release profiles are shown for each granule, it should be understood that such profiles will vary. It is contemplated and within the scope of the invention that other profile shapes may be attained by each granule without departing from the spirit and scope of the invention.

According to one embodiment of the multiple drug release profile formulation of the invention, the gastric release, enteric release and colorectal release granules will act cooperatively to provide a mean steady state plasma concentration level of total DFMO in the range of about 0.1 $\mu$M to about 1000 $\mu$M and preferably in the range of about 1 $\mu$M to 100 $\mu$M and more preferably in the range of about 1 $\mu$M to about 50 $\mu$M.

The gastric, enteric and colorectal release granules of the invention may each be present in a wide range of amounts according to the overall DFMO release profile desired. By way of example and without limitation, it may be desirable to include the granules in the following ratio 1:1:5 parts by weight (gastric: enteric: colorectal release granule) if predominantly direct flooding of the patient by DFMO were desirable, or in the ratio 5:3:2 parts by weight (gastric:enteric:colorectal release granule) if predominantly systemic exposure of the patient to DFMO were more desirable. The exact ratio chosen will depend upon individual patient response to DFMO therapy, toxicity, the extent of cancer progression, the optical form of the DFMO administered, the actual dosage of DFMO in each granule, the desired dosing regimen or the type of cancer being treated.

Generally, each granule will be present in the range of about 1.0 to about 9.0 parts by weight using 10 parts by weight as the basis for the total number of parts by weight which the formulation may contain, i.e. the granules will generally be present in the ratio of about 1.0–9.0: about 1.0–9.0: about 1.0–9.0 parts by weight (gastric:enteric:colorectal release granule).

When the multiple drug release profile formulation of the invention takes the form of a capsule, the gastric, enteric, sustained and colorectal release granules will be found in their entirety enclosed within an outer layer, e.g. hard gelatin capsule, formulated for rapid release.

Methods for the preparation of the dosage forms just mentioned are well known in the art and depend upon whether release of the dosage for core is to be pH-dependent or pH independent, the type of granules within the dosage form, and upon the desire to release the dosage form core contents into the stomach, intestines or colon. Generally and as advantageously employed herein, the dosage form has an outer layer surrounding a core which contents are released into the stomach. A method for preparing such a dosage form generally proceeds as follows. A capsule outer layer comprised of an upper half and a lower half is preformed of a material which is soluble in gastric fluids. The lower half is filled with capsule core contents such as gastric, enteric and colorectal release granules and then capped (sealed) with the upper half to form a capsule dosage form. The relative sizes of the halves as well as the final size of the capsule outer layer generally depend upon the size and weight of the capsule core. One method for the preparation of this formulation is detailed in Example 10.

When the multiple drug release profile formulation of the invention takes the form of a gelcap, caplet or tablet, the gastric, enteric and colorectal release granules may be held together by and coated with an outer layer that dissolves in gastric fluids thereby releasing the granules in the stomach. The outer layer can be a hard gelatin capsule comprised of gelatin, glycerin and sorbitol or other suitable plasticizers.

Pharmaceutical Formulation and Administration

The pharmaceutical formulation of the present invention is intended for oral administration and may be provided in a variety of ways. Any ingredients used in the present formulation should not degrade or decompose a significant portion of the DFMO or other therapeutic compound(s) used prior to administration.

The solid unit dosage form of the invention will comprise DFMO and can be combined with conventional carriers, for example, binders, such as acacia, corn starch or gelatin; disintegrating agents, such as, corn starch, guar gum, potato starch or alginic acid; lubricants, such as, stearic acid or magnesium stearate; and inert fillers, such as lactose, sucrose or corn starch.

The dosage form may also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants and/or tablet polishing agents.

For gelcap preparations, the pharmaceutical formulation may include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides; with alcohols, such as ethanol, isopropanol, hexadecyl alcohol, glycerol and propylene glycol; with glycerol ketals, such as 2,2-dimethyl-1,3-dioxolane-4 methanol; with ethers, such as poly(ethylene glycol) 450, with petroleum hydrocarbons, such as mineral oil and petrolatum; with water, or with mixtures thereof; with or without the addition of a pharmaceutically suitable surfactant, suspending agent or emulsifying agent.

Oils can also be employed in the preparation of formulations of the soft gelatin type. Water, saline, aqueous dextrose and related sugar solutions, and glycerols may be employed in the preparation of suspension formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block poly(oxypropylene) copolymers; and amphoteric detergents, for example, alkyl β-aminopropionates and 2-alkylimidazoline quaternary ammonium salts; and mixtures thereof.

Various other components, not listed above, may be added to the present formulation for optimization of a desired DFMO release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly(vinyl chloride), 1,3-butyleneglycoldimethacrylate, ethyleneglycol dimethacrylate and methacrylate hydrogels.

Since the present formulation may comprise a variety of granules, it is contemplated that a combination of rapid acting, short-acting, fast-releasing, long-acting, gastric release, enteric release, colorectal release, sustained release, controlled release or slow release granules may be used in the present invention.

The course and duration of administration of and the dosage requirements for the formulation of the present invention will vary according to the subject being treated, the formulation used, the method of administration used, the severity and type of cancer being treated, the coadministration of other drugs and other factors.

Although each unit dosage form (capsule, tablet, gelcap or caplet) contains therapeutically effective amounts of DFMO, it may be necessary to administer more than one such unit dosage form in order to obtain the full therapeutic benefit of the DFMO. More particularly, since DFMO may require moderately high doses, vide supra, for preventing and treating colorectal cancer, it is very likely that more than one capsule, tablet, caplet or gelcap will need to be administered to a patient in order to obtain the full therapeutic benefit of DFMO.

For example, consider that the average 70 Kg man has a body surface area of 1.73 m$^2$. If DFMO is administered at a dosage of up to about 3 g/m$^2$/day, then a patient would have to receive about 5 g of DFMO/day, about 10 tablets containing 0.5 g of DFMO. Correspondingly, if the dosage administered is about 0.25 g/m$^2$/day, then a patient would have to receive about 0.4 g/day, about 1 tablet containing 0.5 g of DFMO.

It is intended that the formulation of the invention will maintain DFMO plasma levels within the limits of MTC and MEC for a major portion of the time during which dosage form granules are present in a patient By the term "major portion" is meant at least about 50%.

The therapeutic compound contained within the formulation may be formulated as their pharmaceutically acceptable salts. As used herein, "pharmaceutically acceptable salts" refer to derivatives of the disclosed compounds wherein the parent pharmacologically active compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent pharmacologically active compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two. Generally, nonaqueous media are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention unless the specific stereochemistry or isomer form is specifically indicated. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms.

The racemic and optically pure forms of DFMO may be prepared according to the methods described by Bey et al. (U.S. Pat. No. 4,413,141), Sjoerdsmann et al. (U.S. Pat. No. 4,399,151), Bey et al. (U.S. Pat. No. 4,438,270), ibid (U.S. Pat. No. 4,560,795), ibid (U.S. Pat. No. 10 4,743,691), ibid (U.S. Pat. No. 4,866,206), Au et al. (EP 357029 AZ), Wagner et al. (Anal. Biochem. (1987) 164(1), 102–16), Lindner et al. (J. Liq. Chromatogr. (1986) 9 (2–3), 551–71) and Aldous et al. (J. Chromatogr. (1986) 357(2) 335–9) which references are hereby incorporated in their entirety herein.

The mean steady state plasma concentration level of racemic DFMO can be determined according to the methods described in Smithers (Pharm. Res. (1988) 5, 684–686), Bitonti et al. (Biochem. Pharmacol. (1986), 35, 351–354) and Grove et al. (J. Chromatogr. (1981), 223, 409–416) the disclosures of which are hereby incorporated in their entirety herein.

The mean steady state plasma concentration level of the individual DFMO enantiomers can be determined according to the methods described in Schmitt-Hoffmann (Annual Report of the CIFRE Convention, 1987) the disclosure of which is hereby incorporated in its entirety herein.

EXAMPLE 1

Determination of Racemic DFMO in Plasma

An internal standard (IS), 4-amino-3-hydroxybutyric acid (See FIG. 1 for structure of DFMO and IS) is added to 100 ul of plasma sample. The plasma is deproteinized by the addition of methanol. After centrifugation the supernatant is transferred to a WISP® vial (0.9 mL, designed for the 96 position carousel). Phosphate buffer of pH=7.5 is added to it. DFMO standards in plasma are prepared similarly. The samples and standards are analyzed by pre-column derivatization with 9-phthalaldehyde (OPA). This is accomplished by Water's Auto-Tag technique which uses the WISP® to alternately inject reagent and sample under zero flow conditions. A controller activates the solvent pumps and the reaction mixture is chromatographed by gradient elution. Detection is by fluorescence and data acquisition and calculations are by CALS. A linear curve regression of the peak area ratios of DFMO to IS VS. DFMO concentrations is used to assign concentrations to unknown samples. This procedure is used for the determination of DFMO in plasma over the concentration range of 0.5 to 80 ug/mL. Complete details of the method are described in the appendix.

Materials and Reagents
  Ethanol—absolute, 200 proof, 9A
  Methanol (MeOH)—Burdick & Jackson, glass distilled (B&H)
  Isopropanol (IPA)—(B&J), glass distilled
  acetonitrile (ACN)—(B&J), glass distilled
  0.1M phosphate Buffer, pH=7.5
    (A) 0.1M sodium hydrogen phosphate (Na2HPO4)
    (B) 0.1M sodium dihydrogen phosphate (NaH2PO4)
      (A) and (B) are combined in a ratio of approximately 13 to 3 to give a pH of 7.5
  O-Phthalaldehyde Reagent (OPA)—10.0 mg of o-phthalaldehyde (Sigma Chemical Co.) is dissolved in 1 mL of ethanol. One hundred mcL of 2-mercaptoethanol (Sigma Chemical Co.) and 10 mls of 0.1M phosphate buffer, pH=7.5, is added to the ethanol solution.

Standard Solutions: Eflornithine, MDL 71 782A
  Stock Solution
    Accurately weight 50 mg of compound into a 25 mL volumetric flask and 1.s. with glass distilled water (2 mg/mL).
  Working Solutions A, B, C
    A. Pipette 5 ml of stock solution into a 100 ml volumetric flask and 1.s. with plasma (100 ug/ml).
    B. Pipette 1 ml of stock solution into a 100 ml volumetric flask and q.s. with plasma (20 ug/ml).
    C. Pipette 5 ml of working solution B (above) into a 50 ml volumetric and q.s. with plasma (2 ug/ml).

Internal Standard Solution: 4-Amino-3-hydroxybutyric acid (Aldrich Chemical Co.) Weight 25 mg into a 100 ml volumetric flask and q.s. with glass distilled water.

Equipment
  Centrifuge—Beckman Model TJ-6, Beckman Instrument Co.
  Vortex—Genie Mixer, Scientific Instruments Inc.

Instrumentation
  Analysis are performed on a Waters HPLC System (Millipore, Waters' Chromatography Division) consisting of a Model 720 System Controller, two Model 510 pumps and a WISP\, Model 710B auto-injector. The chromatography column is a Waters' C18, 5 micron, Radial-Pak cartridge, preceded by a pre-column (Upchurch Scientific, Inc.) packed with Waters Bondapak C18/corasil, 37–50 micron particle size. The fluorometer is a Kratos Model FS970 (Schoeffel Instrument Division) operated at an excitation of 335 nm with a 418 nm cut-off filter.

Procedure
I. Preparation of Standard Curve
  1. A series of nine standards, ranging in concentration from 80 to 0.5 mcg/mL, and a blank are prepared as follows:

TABLE 1

| Sample No. | Volume (mL) of Working Std. Solution A, B or C | Volume (mL) of Blank Plasma | Conc. ug/mL |
|---|---|---|---|
| 1 | 4(A) | 1 | 80 |
| 2 | 3(A) | 2 | 60 |
| 3 | 2(A) | 3 | 40 |
| 4 | 5(B) | 0 | 20 |
| 5 | 3(B) | 3 | 10 |
| 6 | 2(B) | 6 | 5 |
| 7 | 5(C) | 0 | 2 |
| 8 | 3(C) | 3 | 1 |
| 9 | 2(C) | 6 | 0.5 |
| 10 | 0 | 5 | 0 |

2. One hundred mL aliquots of each standard are assayed in duplicate. The aliquot is placed in a 13×100 mm test tube.
II. One hundred mcL of sample is placed in a 13×100 mm test tube. The sample is assayed in duplicate.

III. Analysis of Standard and Samples
  A. Sample Preparation
    1. Using a 1.0 mL Hamilton syringe with a PB60 repeating dispenser, add 20 uL (56 ug) of the IS to each standard and sample.
    2. Add 400 uL of methanol and mix on Vortex mixer to insure complete precipitation of proteins.
    3. Centrifuge of 30 minutes at approximately 2,000 rpm.
    4. Remove the supenatant to a 0.9 mL WISP® vial designed for the 96 position carousel. Add 200 uL of 0.02 M phosphate buffer, pH=7.5.
    5. Fill a 0.9 mL WISP® vial with OPA reagent, cap and place in the No. 1 position in the carousel.
    6. Under zero flow conditions 20 ul of OPA reagent is injected followed by 15 uL of sample.
  B. HPLC Operations and Conditions
    Column: Radial-Pak, C18, 5 micron (Nova)
    Pre-column: 2 mm×2 cm, C18/Corasil, 37–50 microns.
    Fluorometer:
      335 nm excitation
      418 nm cut-off filter
    Mobile Phases:
      A. 92% 0.1 M Phosphate, pH=7.5, 5% MeOH, 3% IPA
      B. 80% MeOH, 10% $H_2O$, 5% ACN, 5% IPA
Pump Controller Program

TABLE 2

| Time (min) | Flow Rate (ml/min) | % A | % B | Curve |
|---|---|---|---|---|
| Init | 0 | 80 | 20 | 11 |
| 2 | 0.2 | 80 | 20 | 11 |
| 3 | 1.5 | 80 | 20 | 11 |
| 5 | 1.5 | 80 | 20 | 11 |
| 20 | 1.5 | 80 | 50 | 06 |
| 25 | 1.5 | 80 | 50 | 11 |
| 26 | 1.5 | 80 | 20 | 06 |
| 33 | 0 | 80 | 20 | 11 |

(There is an initial 3 min isocratic flow of 80% A and & 20% B. The flow rate the first minute is 0.2 ml/min. It changes to 1.5 ml/min and remains as such for the rest of the program. The linear gradient is to 50% A, 50% B over 15 min, after which the mobile phase changes to the initial conditions and the column equilibrates for seven minutes before the next injection.)

WISP®

The WISP® is programmed to inject the OPA reagent, in position no. 1 in the carousel, prior to each sample injection. This is accomplished through programming system messages 82 and 72 as 8201 and 7201 (WISP® Operate's Manual, p.4.4, section 4.3.1). The programmed injection times for the OPA reagent and sample are 1 min and 34 min respectively. The sample loop has a 2.0 ml capacity which acts as a mixing chamber for sample and reagent

EXAMPLE 2

Preparation of DFMO-Containing Rapid Release Granule (−)-DFMO (100 g) and microcrystalline cellulose (MCC, AVICEL PH101, 100 g) are mixed thoroughly. A sufficient amount of water to make a wet mass is added to the mixture which is subsequently extruded and spheronized according to well known procedures in the art. The pellets are screened (size 14 to 20 mesh) and dried at 40 C. for 24 hours. Poly(vinyl pyrrolidone) (PVP, 2% by wt of total mass) can optionally be included in the formulation. Increasing PVP will generally lengthen the release profile of the formulation.

EXAMPLE 3

Preparation of DFMO-Containing Slow Release Granule

The granules are prepared similar to Example 9. Thus, DFMO (500 g), MCC (500 g) and EUDRAGIT™ RS 30D (35–50 g) are mixed. To this mixture is added sufficient water to yield a 30% wt. suspension. To the suspension is added TEC (10% wt. based on dry polymer weight of EUDRAGIT™) to yield a dispersion which is wet granulated and dried to remove as much water as possible. The particles are then ground into a fine powder.

EXAMPLE 4

Preparation of DFMO-Containing Capsule Comprising Rapid and Slow Release Granules The following procedure details the preparation of the dosage form described by FIG. 2. Rapid release granules (500 g prepared according to Example 2) and slow release granules (750 g prepared according to Example 3) are thoroughly mixed. The mixture is used to fill 2000 hard gelatin capsules according to procedures well known in the art.

EXAMPLE 5

Preparation of DFMO-Containing Gastric Release Granule

The same method detailed in Example 2 can be employed here to prepare a rapid gastric release granule. Alternatively, a slow gastric release granule can be prepared as follows. DFMO (600 g), MCC (350 g) and HPC (50 g) are mixed thoroughly. To the mixture is added sufficient water to make a wet mass which is extruded and then spheronized using procedures well known in the art. The particles are then dried and ground.

EXAMPLE 6

Preparation of DFMO-Containing Enteric Release Granule

Rapid Release

A latex dispersion is prepared as follows. To EUDRAGIT™ L 30D-55 (1000 g, 15% wt in water) is added a plasticizer (15% wt of dry polymer weight in the EUDRAGIT™) while mixing for 1 to 24 hours. Plasticizers such as triethylcitrate, tributylcitrate, acetyltributylcitrate or dibutylsebacate can be used. To this mixture is added talc (50% wt of dry polymer in the EUDRAGIT™) or glycerylmonostearate (10% wt of dry polymer in the EUDRAGIT™) to form a dispersion. The rapid release granules prepared in Example 2 are coated in a fluidized bed with the latex dispersion until a 10–15% wt increase in granule weight is achieved. The fluidized bed inlet air temperature is adjusted to about 40–45 C. and the outlet air temperature is adjusted to about 30–35 C. with a spray rate of about 2 g/min.

Slow Release

Granules prepared according to Example 3 are coated with EUDRAGIT™ L 30D (10–12% wt.) or AQUATERIC (CAP, 10% wt., plasticized with TEC) until a 25–30% wt. increase in granule weight is achieved.

EXAMPLE 8

Preparation of DFMO-Containing Colorectal Release Granule

Rapid Release

A dispersion is prepared as follows. To EUDRAGIT™ S100 (1000 g, 10% wt in water) is added a plasticizer (10% wt of dry polymer weight in the EUDRAGIT™) while mixing for 1 to 24 hrs. Plasticizers such as triethylcitrate, tributylcitrate, acetyltributylcitrate or dibutylsebacate can be used. To this mixture is added talc (50% wt of dry polymer in the EUDRAGIT™) to form a dispersion. The rapid release granules prepared in Example 2 are coated in a fluidized bed with this dispersion until a 15% wt increase in granule weight is achieved.

Slow Release

A mixture is prepared as follows. EUDRAGIT™ RS 30D (1000 g, 15% wt. aqueous dispersion, AQUA-COAT™ OR SURELEASE) is plasticized with triethylcitrate (TEC, 20% wt. of dry polymer in the EUDRAGIT™) for 1–24 hours. Talc (50% wt of dry polymer in the EUDRAGIT™) is added with mixing to form the mixture. The rapid release granules prepared in Example 2 are coated with this mixture until a 10–15% wt. increase in granule weight is achieved. The coated granules are then coated with an EUDRAGIT™ S100 dispersion as done immediately above until a 10–15% wt. increase in granule weight is achieved.

EXAMPLE 9

Preparation of DFMO-Containing Sustained Release Granule

This procedure employs a double granulation. Thus, DFMO (500 g), MCC (500 g) and EUDRAGIT™ RS 30D (75–100 g) are mixed. To this mixture is added sufficient water to yield a 30% wt. suspension. To the suspension is added TEC(10% wt. based on dry polymer weight of EUDRAGIT™) to yield a dispersion which is wet granulated and dried to remove as much water as possible. The granules are then ground into a fine powder. To the powder is added sufficient water to make a wet mass which is extruded, spheronized, dried, ground and screened (size 14–20 mesh).

EXAMPLE 10

Preparation of DFMO-Containing Capsule Comprising Gastric Enteric and Colorectal Release Granules The following procedure details the preparation of the dosage form described by FIG. 5. Rapid gastric release granules (450 g, prepared according to Example 2), rapid enteric release granules (100 g, prepared according to Example 6) and slow colorectal release granules (450 g, prepared according to Example 8) are mixed thoroughly. Hard gelatin capsules (2000) are then filled with the mixture using procedures and equipment well known in the art.

EXAMPLE 11

Figure 12:
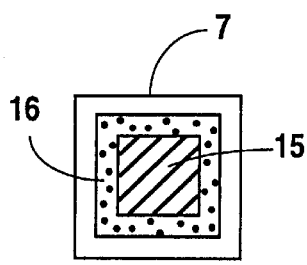
FIG. 12. Cross-sectional view of a first tablet dosage form of the sustained release formulation embodiment of the invention. 15=drug in matrix core for slow delivery to the GI tract; 16=drug in priming dose in HPMC or similar rapid release coating.
Figure 13:
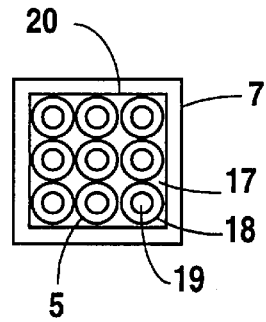
FIG. 13. Cross-sectional view of a second tablet dosage form containing sustained release coated pellets in a rapidly disintegrating tablet compact. 19=rapid release pellet; 18=sustained release coating (EUDRAGIT™ S100 or EUDRAGIT™ 4110D); 17=tablet granulation containing DFMO for immediate release and absorption; 20=compressed tablet.

Preparation of DFMO-Containing Tablets Comprising Rapid and Slow Colorectal Release Granules The following procedure details the preparation of the dosage form described by FIG. 12 and comprises a slow release core surrounded by a rapid release layer which is then surrounded by a pH responsive coating for colorectal release. Thus, DFMO (600 g) is dry blended with AVICEL PH101 (260 g), PVP (30 g), HMPC (100 g, K15M), fumed silicon dioxide (50 g, CAB-O-SIL M5P), and magnesium stearate (50 g). The mixture is then compressed into tablets. HPMC (70–80 g, aqueous coat, Opadry®, plasticized with propylene glycol) and DFMO (20–30 g) are mixed and turned into a dispersion by the addition of water. The tablets just prepared are coated with the HPMC/DFMO dispersion until the desired tablet weight gain has been achieved to form a two layered tablet. The layered tablet is then coated in a perforated pan coating unit with EUDRAGIT™ S100 until a 15% wt. increase in tablet weight is achieved.

EXAMPLE 12

Pellet Formulation

The present example is provided to demonstrate the utility of the present invention for the preparation of pellets.

TABLE 3

| Compound | % (w/w) |
| --- | --- |
| Eflornithine Hydrochloride Lot # A1981-004 | 50 |
| Avicel ® PH101 | 47 |
| Kollidon ® K90 | 3 |
| Total | 100 |

Procedure a. Kollidon® K90 prepared as a 10% w/w aqueous solution with distilled water.

b. Particle size of bulk drug reduced with porcelain mortar and pestle and dry blended for 10 minutes with Avicel® PH101.

c. Powder blend transferred to a planetary mixer and the Kollidon® K90 solution slowly added.

d. An additional aliquot of approximately 5% to 13% (based on dry weight of formulation) of distilled water was added to the powder/PVP mass to achieve desirable wet massing.

e. Final wet mass allowed to mix for an additional 3–5 minutes.

1. Extrusion

Procedure a. Extrusion of the wet mass in Table 3 was accomplished using a bench top extruder fitted with a 1.0 mm screen.

b. The rotation speed was set at maximum (approximately 25 rpm).

c. The extruded strands were collected periodically and processed further.

2. Spheronization

Procedure a. Spheronization was accomplished using a bench top spheronizer fitted with a fine cut plate.

b. An aliquot of approximately 100–150 gm of extruded material was charged into the chamber and spheronized as indicated below.

c. Periodic dusting of the pellets with Avicel® PH101 was done to absorb expired moisture produced during the spheronization in order to reduce particle adhesion and limit particle growth.

d. The wet pellets were collected and gently screened through a 14 and 18 mesh screen to remove fines and oversized particles. The under/over sized material was recycled into the extrusion mass to increase yield and decrease waste.

e.

TABLE 4

Spheronization Time/Speed

| Time (min) | Percent of Maximum |
|---|---|
| 1 | 50% |
| 1 | 75% |
| 2–3 | 100% |
| Total Spheronization Time | 4–5 min |

3. Collection and Sizing

Procedure a. The wet pellets were collected and evenly spread onto aluminum sheets.

b. These sheets were then placed in 40° C. ovens, and the pellets were allowed to dry overnight.

c. The dried pellets were collected and vacuumed dusted to remove any free particulate matter.

d. The final bead distribution was assessed using standard metal screens and is shown below.

e. The percent of lost material in processing was less than 3%.

f. Pellets of the 16–18 mesh and 18–20 mesh size were blended and used in subsequent procedures.

TABLE 5

Pellet Size Distribution

| Pass Through (mesh) | Retained On (mesh) | % of Starting Material |
|---|---|---|
| 12 | 16 | 19.7 |
| 16 | 18 | 54.9 |
| 18 | 20 | 16.4 |
| 20 | 30 | 6.2 |
| | Total | 97.2 |

4. Pellet Coating

Equipment a. All coatings were applied with using a fluidized bed coater fitted with a Wurster insert and a bottom spray technique. A filter bag assembly was used, and the insert adjusted from ⅜" to ½" above the floor of the coating chamber in order to obtain a desirable flow of pellets through the spray path.

b. Coating material was supplied with a peristalic pump and the spray rate adjusted as indicated.

c. The atomization pressure was 0.8–1.2 bar, and the filter blow out pressure was set at 1–2 bar.

d. The coating charge unless otherwise stated was 300 gm of size 16–20 mesh pellets as indicated above.

Enteric Coating

TABLE 6

Coating Formulation

| Material | Based On | Weight |
|---|---|---|
| EUDRAGIT ™ L30D-55 | | 87.00 gm |
| Triethyl Citrate (TEC) | 15%, dry weight polymer | 3.92 gm |
| Talc | 50%, dry weight polymer | 13.05 gm |
| Water | Total solids to be 15% | 196.18 gm |
| | Total Suspension Weight | 300.15 gm |

Calculation

For an 8% weight gain of polymer (x is dry weight of polymer)

$$\frac{x}{300+x} = 0.08$$

where x is 26.1 gm and is provided by 87.00 gm of 30% polymer suspension.

Procedure a. The EUDRAGIT™ L30D-55 and TEC were combined and allowed to stir for 30 minutes.

b. The talc was separately dispersed in the water for 10 minutes at 4500 rpm.

c. The talc suspension was added with stirring to the EUDRAGIT™/TEC suspension.

TABLE 7

Spray Process

| Time (min) | Spray Rate (g/min) | Temperature (° C.) In/Out | Air Volume (M³/H) |
|---|---|---|---|
| 5 | 0 | 45/33 | 50 |
| 15 | 1.5 | 40/32 | 60 |
| 130 | 2.5 | 40/30 | 50–60 |

Curing a. Coated beads were collected and spread evenly onto aluminum sheets.

b. Final product allowed to dry at room temperature overnight.

Colonic Coating

TABLE 8

Coating Formulation

| Material | Based On | Weight |
|---|---|---|
| EUDRAGIT ™ 4110D | | 87.00 gm |
| Triethyl Citrate (TEC) | 5%, dry weight polymer | 1.3 gm |
| Imwitor ® 900 | 5%, dry weight polymer | 1.3 gm |
| Water | Total solids to be 15% | 93.1 gm |
| | Total Suspension Weight | 182.7 gm |

Calculation

For an 8% weight gain of polymer (x is dry weight of polymer)

$$\frac{x}{300+x} = 0.08$$

where x is 26.1 gm and is provided by 87.00 gm of 30% polymer suspension.

Procedure
a. The TEC, Imwitor® 900, and water are heated to approximately 65° C. and then homogenized at 4000 rmp for 15 minutes. The resultant dispersion is then allowed to cool to less than 30° C. before adding to the EUDRAGIT™ 4110D.
b. The final dispersion is allowed to stir for 15 minutes prior to application.

TABLE 9

Spray Process

| Time (min) | Spray Rate (g/min) | Temperature (° C.) In/Out | Air Volume ($M^3/H$) |
|---|---|---|---|
| 5 | 0 | 30/27 | 50 |
| 15 | 2.0 | 33/26 | 50 |
| 65 | 2.5 | 36/26 | 50 |

Curing
a. Coated beads were collected and spread evenly onto aluminum sheets.
b. Final product allowed to dry at room temperature overnight.

Extended Release Coating

TABLE 10

Coating Formulation

| Material | Based On | Weight |
|---|---|---|
| EUDRAGIT ™ RS30D | | 100.00 gm |
| EUDRAGIT ™ RL30D | | 11.10 gm |
| Triethyl Citrate (TEC) | 15%, dry weight polymer | 5.00 gm |
| Imwitor ® 900 | 5%, dry weight polymer | 1.67 gm |
| Water | Total solids to be 15% | 115.40 gm |
| | Total Suspension Weight | 233.13 gm |

Calculation
For a 10% weight gain of polymer (x is dry weight of polymer)

$$\frac{x}{300+x} = 0.1$$

where x is 33.3 gm and is provided by 111.10 gm of 30% polymer suspension in a ratio of 9:1 RS30D to RL30D.

Procedure
a. The TEC, Imwitor® 900, and water are heated to approximately 65° C. and then homogenized at 4000 rpm for 15 minutes. The resultant dispersion is then allowed to cool to less than 30° C. before adding to the EUDRAGIT™ RS/RL dispersion.
b. The final dispersion is allowed to stir for 15 minutes prior to application.

TABLE 11

Spray Process

| Time (min) | Spray Rate (g/min) | Temperature (° C.) In/Out | Air Volume ($M^3/H$) |
|---|---|---|---|
| 5 | 0 | 35/32 | 25 |
| 115 | 2.1–2.3 | 38/29 | 70 |
| 15 | 0 | 38/38 | 70 |

Curing
1. Coated beads were dried in situ for 15 minutes with the filter screen in place in preparation for the next application.

Colonic Coating of Extended Release Pellets

TABLE 12

Coating Formulation

| Material | Based On | Weight |
|---|---|---|
| EUDRAGIT ™ 4110D | | 95.70 gm |
| Triethyl Citrate (TEC) | 5%, dry weight polymer | 1.40 gm |
| Imwitor ® 900 | 5%, dry weight polymer | 1.40 gm |
| Water | Total solids to be 15% | 102.20 gm |
| | Total Suspension Weight | 200.70 gm |

Calculation
For a 8% weight gain of polymer (x is dry weight of polymer)

$$\frac{x}{300+x} = 0.08$$

where x is 28.7 gm and is provided by 95.70 gm of 30% polymer suspension. Here, the coating charge is increased due to the weight gain of solid material from the previous spray application.

Procedure
a. The TEC, Imwitor® 900, and water are heated to approximately 65° C. and then homogenized at 4000 rmp for 15 minutes. The resultant dispersion is then allowed to cool to less than 30° C. before adding to the EUDRAGIT™ 4110D dispersion.
b. The final dispersion is allowed to stir for 15 minutes prior to application.

TABLE 13

Spray Process

| Time (min) | Spray Rate (g/min) | Temperature (° C.) In/Out | Air Volume ($M^3/H$) |
|---|---|---|---|
| 5 | 0 | 35/30 | 70 |
| 65 | 2.1–2.5 | 38/29 | 70 |

Beads were immediately coated with a 0.2% Imwitor® 900 top coat to prevent sticking during drying and storage.

0.2% GMS Top Coat

TABLE 14

Coating Formulation

| Material | Based On | Weight |
|---|---|---|
| Imwitor ® 900 | | 0.70 gm |
| Water | Total solids to be 2% | 34.30 gm |
| | Total Suspension Weight | 35.00 gm |

Calculation
For a 0.2% weight gain of polymer (x is dry weight of polymer)

$$\frac{x}{350+x} = 0.002$$

where x is 0.7 gm. Here, the coating charge is increased due to the weight gain of solid material from the previous spray applications.

Procedure

1. The Imwitor® 900, and water are heated to approximately 65° C. and then homogenized at 4000 rpm for 15 minutes.

TABLE 15

Spray Process

| Time (min) | Spray Rate (g/min) | Temperature (° C.) In/Out | Air Volume (M³/H) |
|---|---|---|---|
| 3 | 0 | 39/33 | 70 |
| 15 | 2.1–2.5 | 39/30 | 70 |
| 10 | 0 | 40/40 | 70 |

Curing a. Coated beads were collected and spread evenly onto aluminum sheets.

Final product allowed to dry at room temperature over the weekend.

Dissolution Testing

Apparatus b. Testing was done using the USP Method II, rotating paddle procedure.
c. All testing was done at 37° C. and 100 rpm paddle speed.
d. Various dissolution media was used to approximate the in vivo conditions that the pellets may experience.
e. Three milliliter samples were drawn at set time points, and blank dissolution media was added to maintain a constant dissolution volume.
f. Final dissolution volumes were 500 ml except for testing of the EUDRAGIT™ L30D-55 product where the final volume was 467 ml.
g. Initial media was 0.1 N HCL and, if needed, aliquots of 0.2 M sodium phosphate tribasic was added to increase the pH. At pH changes after the addition of the 0.2 M sodium phosphate, the pH of the individual kettles was adjusted with 2 M HCL or 2 M NaOH prior to sampling.
h. Dissolution samples were filtered with a 0.45 pm PTFE filter prior to analysis.

TABLE 16

Dissolution Time and Media

| Product | Time | Media | pH |
|---|---|---|---|
| Uncoated Pellets | 0–120 min | 0.1 N HCl 500 ml | 1.0 |
| EUDRAGIT™ L30D055 | 0–120 min | 0.1 N HCl 350 ml | 1.0 |
| | 120–165 min | +117 ml 0.2 M NaPO | 6.8 |
| EUDRAGIT™ 4110D | 0–120 min | 0.1 N HCl 375 ml | 1.0 |
| | 120–240 min | +87.5 ml 0.2 M NaPO | 6.0 |
| | 240–360 min | +37.5 ml 0.2 M NaPO | 7.4 |
| EUDRAGIT™ RS/RL w/ EUDRAGIT™ 4110D | 0–120 min | 0.1 N HCl 375 ml | 1.0 |
| | 120–240 min | +87.5 ml 0.2 M NaPO | 6.0 |
| | 240–870 min | +37.5 ml 0.2 M NaPO | 7.4 |

5. Drug Content

Procedure a. An aliquot of pellets was ground with a porcelain mortar and pestle.
b. Approximately 500 mg aliquot of the ground material was transferred to a 250 ml volumetric flask and brought to ¾ volume with distilled water.
c. The flasks were then sonicated for 20 minutes and allowed to cool to room temperature before bringing up to volume with distilled water.
d. Sample aliquots were filtered with a 10 pm and then a 0.45 pm filter prior to analysis.

EXAMPLE 13

Pellet Formulation Rapid Release Core Pellet and Enteric Polymer Coated Pellet

The present example is provided to demonstrate the DFMO release profile of an uncoated rapid release pellet. The dissolution profile of this formulation is demonstrated at FIG. 14.

TABLE 17

Pellet Formulation

| Compound | % (w/w) |
|---|---|
| Eflornithine Hydrochloride Lot #A1931-004 | 50 |
| Avicel® PH101 | 47 |
| Kollidon® K90 | 3 |
| Total | 100 |

Figure 14:
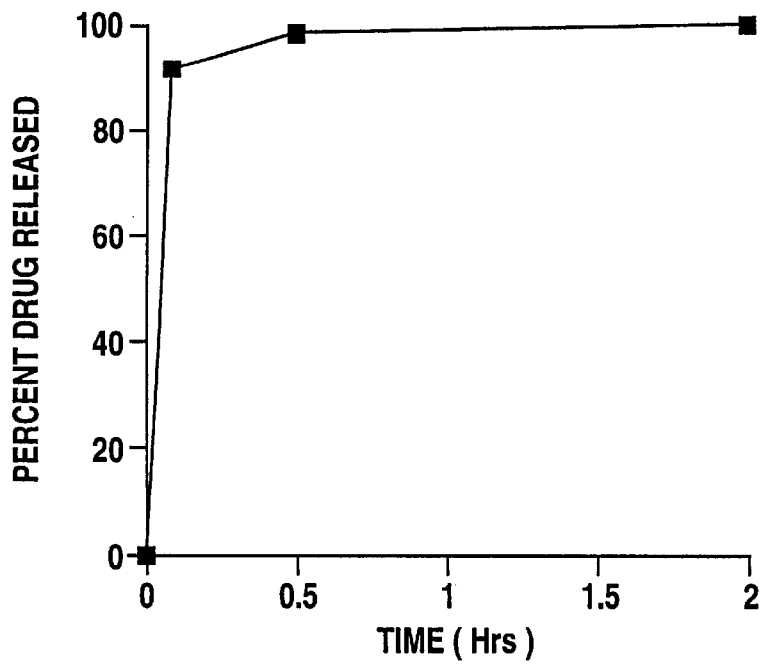
FIG. 14. Dissolution profile of uncoated rapid release pellets in 500 ml, 0.1 N HCl using the USP method II.

The particle size distribution of the dried extruded pellets is shown in Table 19. FIG. 14 shows the DFMO is rapidly released, with over 90% of the drug being released within 5 minutes when placed in 0.1 N HCl. (uncoated=(-■-) (see FIG. 14).

Procedure

1. Kollidon® K90 prepared as a 10% w/w aqueous solution with distilled water.
2. Particle size of bulk drug reduced with porcelain mortar and pestle and dry blended for 10 minutes with Avicel® PH101.
3. Powder blend transferred to a planetary mixer and the Kollidon® K90 solution slowly added.
4. An additional aliquot of approximately 5% to 13% (based on dry weight of formulation) of distilled water was added to the powder/PVP mass to achieve desirable wet massing.
5. Final wet mass allowed to mix for an additional 3–5 minutes.

Extrusion

Procedure

1. Extrusion of the wet mass was accomplished using a bench top extruder fitted with a 1.0 mm screen.
2. The rotation speed was set at maximum (approximately 25 rpm).
3. The extruded strands were collected periodically and processed further.

Spheronization

1. Spheronization was accomplished using a bench top spheronizer fitted with a fine cut plate.
2. An aliquot of approximately 100–150 gm of extruded material was charged into the chamber and spheronized as indicated below.

3. Periodic dusting of the pellets with Avicel® PH101 was done to adsorb expired moisture produced during the spheronization in order to reduce particle adhesion and limit particle growth.
4. The wet pellets were collected and gently screened through a 14 and 18 mesh screen to remove fines and oversized particles. The under/over sized material was recycled into the extrusion mass to increase yield and decrease waste.

TABLE 18

Spheronization Time/Speed

| Time (min) | Percent of Maximum |
|---|---|
| 1 | 50% |
| 1 | 75% |
| 2–3 | 100% |
| Total Spheronization Time | 4–5 min |

Collection and Sizing

Procedure

1. The wet pellets were collected and evenly spread onto aluminum sheets.
2. These sheets were then placed in 40° C. ovens, and the pellets were allowed to dry overnight.
3. The dried pellets were collected and vacuumed dusted to remove any free particulate matter.
4. The final bead distribution was assessed using standard metal screens and is shown below.
5. The percent of lost material in processing was less than 3%.
6. Pellets of the 16–18 mesh and 18–20 mesh size were blended and used in subsequent procedures.

TABLE 19

Pellet Size Distribution

| Pass Through (mesh) | Retained On (Mesh) | % of Starting Material |
|---|---|---|
| 12 | 16 | 19.7 |
| 16 | 18 | 54.9 |
| 18 | 20 | 16.4 |
| 20 | 30 | 6.2 |
| Total | | 97.2 |

The following formula was employed to prepare the pellets coated with an enteric polymer of the present invention.

Figure 15:
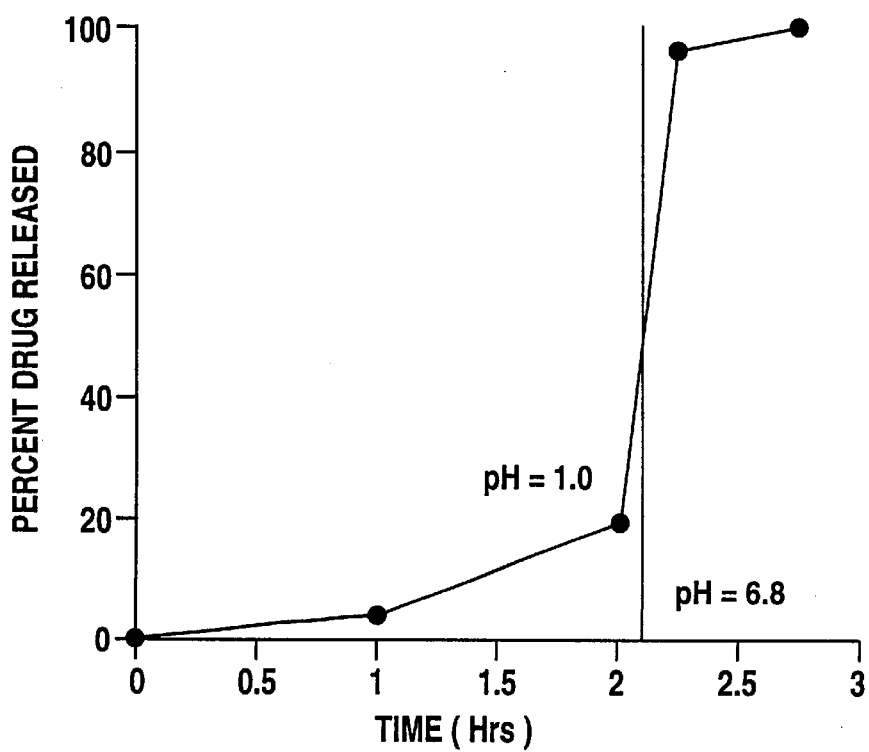
FIG. 15. Dissolution profile in pH 1.0 and 6.8 of rapid release DFMO pellets coated with 8% EUDRAGIT™ L30D 55.

As demonstrated in FIG. 15, release of the active ingredient DFMO was less than 10% after 1 hour and less than 20% after 2 hours. These release rates could be decreased with higher levels of polymer being applied to the pellets.

The profile mirrors the delayed plasma level drug (DFMO) illustrated in FIG. 1, middle profile (Rapid enteric release).

Pellet Coating

Equipment

1. All coatings were applied with using a fluidized bed coater fitted with a Wurster insert and a bottom spray technique.
2. Coating material was supplied with a peristaltic pump and the spray rate adjusted as indicated.
3. The atomization pressure was 0.8–1.2 bar, and the filter blow out pressure was set at 1–2 bar.
4. The coating charge unless otherwise stated was 300 gm of size 16–20 mesh pellets as indicated above.

Enteric Coating

TABLE 20

Coating Formulation

| Material | Based On | Weight |
|---|---|---|
| EUDRAGI ™ L30D-55 | | 87.00 gm |
| Triethyl Citrate (TEC) | 15%, dry weight polymer | 3.92 gm |
| Talc | 50%, dry weight polymer | 13.05 gm |
| Water | Total solids to be 15% | 196.18 gm |
| Total Suspension Weight | | 300.15 gm |

Calculation

For an 8% weight gain of polymer (x is dry weight of polymer)

$$\frac{x}{300+x} = 0.08$$

where x is 26.1 gm and is provided by 87.00 gm of 30% polymer suspension.

Procedure

1. The EUDRAGIT™ L30D-55 and TEC were combined and allowed to stir for 30 minutes.
2. The talc was separately dispersed in the water for 10 minutes at 4500 rpm.
3. The talc suspension was added with stirring to the EUDRAGIT™/TEC suspension.

TABLE 21

Spray Process

| Time (min) | Spray Rate (g/min) | Temperature (° C.) In/Out | Air Volume (M³/H) |
|---|---|---|---|
| 5 | 0 | 45/33 | 50 |
| 15 | 1.5 | 40/32 | 60 |
| 130 | 2.5 | 40/30 | 50–60 |

Curing

1. Coated beads were collected and spread evenly onto aluminum sheets.
2. Final product allowed to dry at room temperature overnight.

FIG. 15 illustrates that with 8% weight gain of EUDRAGIT™ L30D-55, less than 20% of the drug was released in acidic medium. Rapid drug release was evident when the medium was changed to pH 6.8.

Colonic Coating

TABLE 22

Coating Formulation

| Material | Based On | Weight |
|---|---|---|
| EUDRAGIT ™ 4110D | | 87.00 gm |
| Triethyl Citrate (TEC) | 5%, dry weight polymer | 1.3 gm |
| Imwitor ® 900 | 5%, dry weight polymer | 1.3 gm |
| Water | Total solids to be 15% | 93.1 gm |
| Total Suspension Weight | | 182.7 gm |

Calculation

For an 8% weight gain of polymer (x is dry weight of polymer)

$$\frac{x}{300+x} = 0.08$$

where x is 26.1 gm and is provided by 87.00 gm of 30% polymer suspension.

Procedure
1. The TEC, Imwitor® 900, and water are heated to approximately 65° C. and then homogenized at 4000 rpm for 15 minutes. The resultant dispersion is then allowed to cool to less than 30° C. before adding to the EUDRAGIT™ 4110D.
2. The final dispersion is allowed to stir for 15 minutes prior to application.

TABLE 23

Spray Process

| Time (min) | Spray Rate (g/min) | Temperature (° C.) In/Out | Air Volume (M³/H) |
|---|---|---|---|
| 5 | 0 | 30/27 | 50 |
| 15 | 2.0 | 33/26 | 50 |
| 65 | 2.5 | 36/26 | 50 |

Curing
1. Coated beads were collected and spread evenly onto aluminum sheets.
2. Final product allowed to dry at room temperature overnight.

Figure 16:
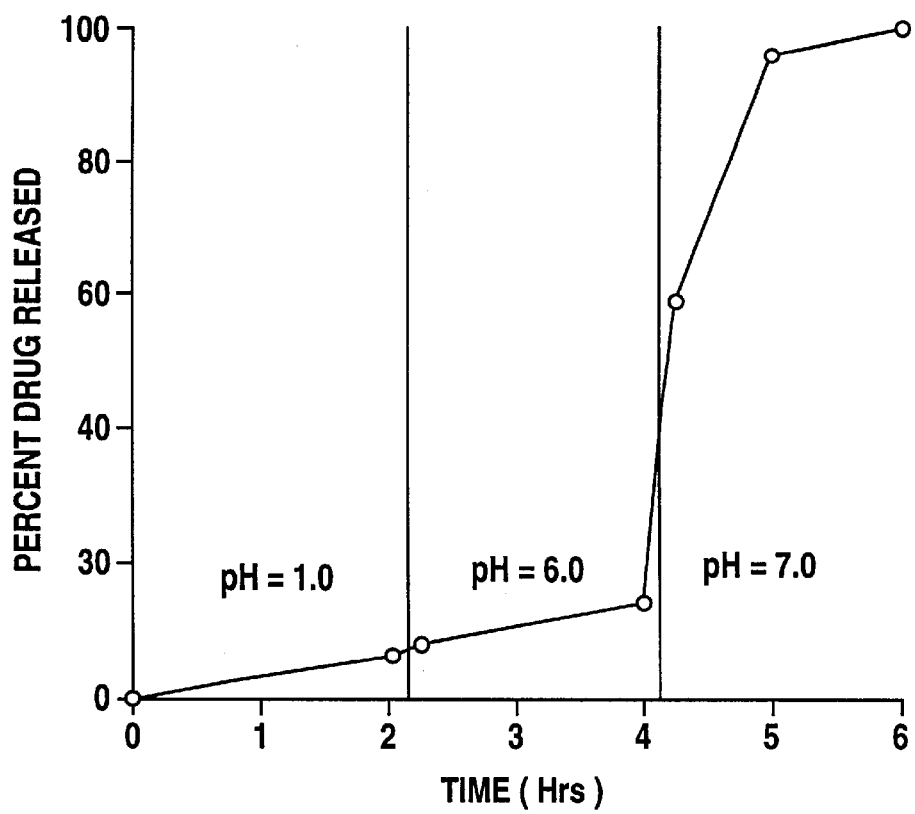
FIG. 16. Influence of pH on the dissolution properties of rapid release DFMO pellets coated with EUDRAGIT™ 4110D.

The DFMO release profile of the colonic coating preparation (third peak) (-O-O-O-) is further illustrated in FIG. 16. In FIG. 16 it is demonstrated that less than 20% of the drug was released after 4 hours when the coated pellets were first subjected to pH media 1.0 for 2 hours, and then followed by pH media 6.0 for 2 hours. Since EUDRAGIT™ 4110D starts to dissolve at pH 6.8, rapid release of the drug was seen when the pH of the media was adjusted to pH 7.4. The anticipated plasma blood level profile is represented in the far right profile of FIG. 1 (open circles, -O-O-O-).

EXAMPLE 14

Extended Release Coating

To extend the release profile of this very water-soluble drug (DFMO) in the colon, an extended release coating was applied to the pellets.

TABLE 24

Extended Release Coating Formulation

| Material | Based On | Weight |
|---|---|---|
| EUDRAGIT ™ RS30 | | 100.00 gm |
| EUDRAGIT ™ RL30D | | 11.10 gm |
| Triethyl Citrate (TEC) | 15%, dry weight polymer | 5.00 gm |
| Imwitor ® 900 | 5%, dry weight polymer | 1.67 gm |
| Water | Total solids to be 15% | 115.40 gm |
| Total Suspension Weight | | 233.13 gm |

Calculation

For a 10% weight gain of polymer (x is dry weight of polymer)

$$\frac{x}{300+x} = 0.1$$

where x is 33.3 gm and is provided by 111.10 gm of 30% polymer suspension in a ratio of 9:1 RS30D to RL30D.

Procedure
1. The TEC, Imwitor® 900, and water are heated to approximately 65° C. and then homogenized at 4000 rpm for 15 minutes. The resultant dispersion is then allowed to cool to less than 30° C. before adding to the EUDRAGIT™ RS/RL dispersion.

TABLE 25

Spray Process

| Time (min) | Spray Rate (g/min) | Temperature (° C.) In/Out | Air Volume (M³/H) |
|---|---|---|---|
| 5 | 0 | 35/32 | 25 |
| 115 | 21–23 | 38/29 | 70 |
| 15 | 0 | 38/38 | 70 |

Curing
1. Coated beads were dried in situ for 15 minutes with the filter screen in place in preparation for the next application.

Colonic Coating of Extended Release Pellets
Coat #2 (Outside Coat)

TABLE 26

Coating Formulation

| Material | Based On | Weight |
|---|---|---|
| EUDRAGIT ™ 4110D | | 95.70 gm |
| Triethyl Citrate (TEC) | 5%, dry weight polymer | 1.40 gm |
| Imwitor ® 900 | 5%, dry weight polymer | 1.40 gm |
| Water | Total solids to be 15% | 102.20 gm |
| Total Suspension Weight | | 200.70 gm |

This coat protects the pellet in the GI tract until a pH of greater than 6.8 is achieved. At that pH and above, the 4110D begins to dissolve.

Calculation

For an 8% weight gain of polymer (x is dry weight of polymer)

$$\frac{x}{300+x} = 0.08$$

where x is 28.7 gm and is provided by 95.70 gm of 30% polmer suspension. Here, the coating charge is increased due to the weight gain of solid material from the previous spray application.

Procedure
1. The TEC, Imwitor® 900, and water are heated to approximately 65° C. and then homogenized at 4000 rpm for 15 minutes. The resultant dispersion is then allowed to cool to less than 30° C. before adding to the EUDRAGIT™ 4110D dispersion.
2. The final dispersion is allowed to stir for 15 minutes prior to application.

TABLE 27

Spray Process

| Time (min) | Spray Rate (g/min) | Temperature (° C.) In/Out | Air Volume (M³/H) |
|---|---|---|---|
| 5 | 0 | 35/30 | 70 |
| 65 | 2.1–2.5 | 38/29 | 70 |

Beads were immediately coated with a 0.2% Imwitor® 900 top coat to prevent sticking during drying and storage.
0.2% GMS Top Coat

TABLE 28

Coating Formulation

| Material | Based On | Weight |
|---|---|---|
| Imwitor ® 900 | | 0.70 gm |
| Water | Total solids to be 2% | 34.30 gm |
| | Total Suspension Weight | 35.00 gm |

Calculation
For a 0.2% weight gain of polymer (x is dry weight of polymer)

$$\frac{x}{300+x} = 0.002$$

where x is 0.7 gm. Here, the coating charge is increased due to the weight gain of solid material from the previous spray applications.

Procedure
1. The Imwitor® 900, and water are heated to approximately 65° C. and then homogenized at 4000 rpm for 15 minutes.

TABLE 29

Spray Process

| Time (min) | Spray Rate (g/min) | Temperature (° C.) In/Out | Air Volume (M³/H) |
|---|---|---|---|
| 3 | 0 | 39/33 | 70 |
| 15 | 2.1–2.5 | 39/30 | 70 |
| 10 | 0 | 40/40 | 70 |

Curing
1. Coated beads were collected and spread evenly onto aluminum sheets.
2. Final product allowed to dry at room temperature over the weekend.

Figure 17:
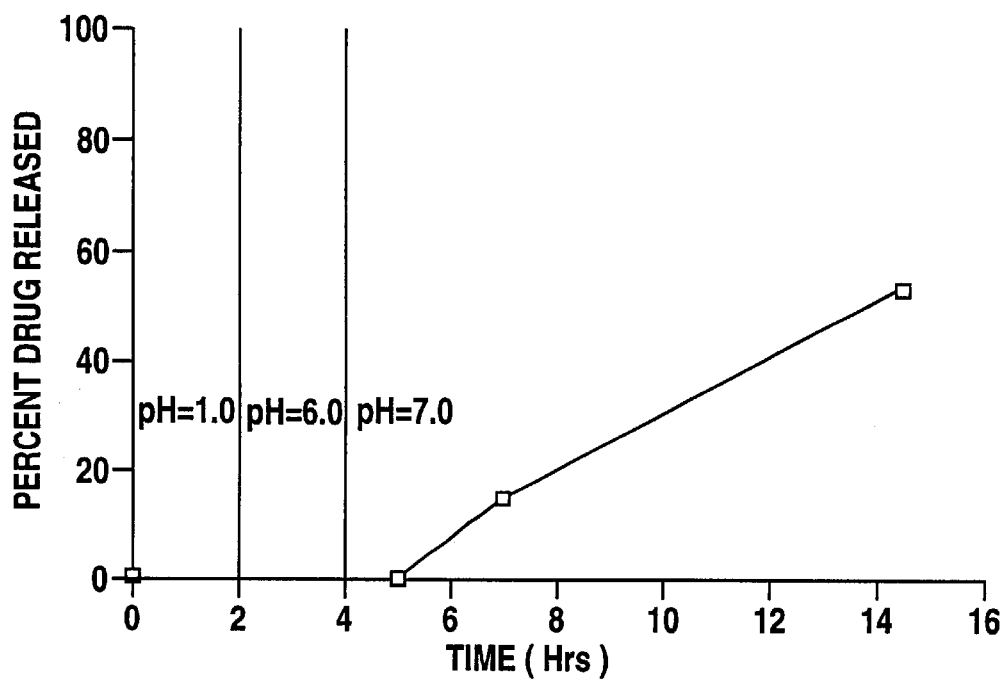
FIG. 17. Influence of pH on the release of DFMO from rapid release, DFMO core pellets coated first with 10% EUDRAGIT™ RS/RL30D (9:1) and then 8% EUDRAGIT™ 4110D as presented as open squares (-□-□-□-).

As shown in FIG. 17, drug release from the extended release pellet formulations coated with EUDRAGIT™ 4110D did not release drug during the first 5 hours that the pellets were exposed to pH 1.0, 6.0, and then 7.0 after 7 hours, approximately 17% of the drug was released and after about 14½ hours, approximately 55% of the drug was released from the pellets. In FIG. 2, a pellet coated with a combination of RS30 and RL30D and a top coat of 4110D (-◇-◇-◇-) is represented in an expected in vivo blood release profile of DFMO. A rapid release pellet coated with 4110D is illustrated in FIG. 2, open circles. The subcoat of the various pharmaceutical preparations described herein may include other materials with properties of EUDRAGIT™ 4110D, that would produce similiar results. Such would include materials that dissolve or disintegrate above pH 6.8. By example, these are EUDRAGIT™ S100 or HPMC acetate succinate derivative, and polyanhydrides and other retardant materials that are broken down or degraded by enzymes and bacteria in the colon.

Dissolution Testing
Apparatus
1. Testing was done using the USP Method II, rotating paddle procedure.
2. All testing was done at 37° C. and 100 rpm paddle speed.
3. Various dissolution media was used to approximate the in vivo conditions that the pellets may experience.
4. Three milliliter samples were drawn at set time points, and blank dissolution media was added to maintain a constant dissolution volume
5. Final dissolution volumes were 500 ml except for testing of the EUDRAGIT™ L30D-55 product where the final volume was 467 ml.
6. Initial media was 0.1 N HCL and, if needed, aliquots of 0.2 M sodium phosphate tribasic was added to increase the pH. At pH changes after the addition of the 0.2 M sodium phosphate, the pH of the individual kettles was adjusted with 2 Mm HCL or 2 M NaOH prior to sampling.

TABLE 30

Dissolution Time and Media

| Product | Time | Media | pH |
|---|---|---|---|
| Uncoated Pellets | 0–120 min | 0.1N HCl 500 ml | 1.0 |
| EUDRAGIT ™ L30D-55 | 0–120 min | 0.1N HCl 350 ml | 1.0 |
| | 120–165 min | +117 ml 0.2M NaPO₄ | 6.8 61 |
| EUDRAGIT ™ 4110D | 0–120 min | 0.1N HCl 375 ml | 1.0 |
| | 120–240 min | +87.5 ml 0.2M NaPO₄ | 6.0 |
| | 240-360 min | +37.5 ml 0.2M NaPO₄ | 7.4 |
| EUDRAGIT ™ RS/RL w/ EUDRAGIT ™ 4110D | 0–120 min | 0.1N HCl 375 ml | 1.0 |
| | 120–240 min | +87.5 ml 0.2M NaPO₄ | 6.0 |
| | 240–870 min | +37.5 ml 0.2M NaPO₄ | 7.4 |

Drug Content
Procedure
1. An aliquot of pellets was ground with a porcelain mortar and pestle.
2. Approximately 500 mg aliquot of the ground material was transferred to a 250 ml volumetric flask and brought to 3/4 volume with distilled water.
3. The flasks were then sonicated for 20 minutes and allowed to cool to room temperature before bringing up to volume with distilled water.
4. Sample aliquots were filtered with a 10 $\mu$m and then a 0.45 $\mu$m filter prior to analysis.

Drug Analysis
HPLC Conditions
Column: Rainin Microsorb™ Short-One® C18, ODS-1, 3 $\mu$m
Mobile Phase: 1.1 mM Sodium Dodecyl Sulfate in 23/77 Acetonitrile/0.039 M NaPO₄ (pH=2.3)
Flow Rate: 1.0 ml/min
Detection: 210 nm
Injection Volume: 50 $\mu$l
Retention Time: 4.5 minutes

EXAMPLE 15

DFMO-Containing Slow Release Matrix Pellets— No Coating

The present example is provided to demonstrate the utility of the present formulation in providing a slow release matrix pellet formulation of DFMO.

I. Pellet Formulation

TABLE 31

| Compound | % (w/w) |
| --- | --- |
| Eflornithine Hydrochloride Lot #R41063 | 46.9 |
| Avicel ® RC591 | 10.4 |
| Sterotex K | 26.1 |
| EUDRAGIT ™ NE40D (dry polymer) | 16.6 |
| Total | 100 |

Procedure
1. Aggregates of bulk drug were reduced with a porcelain mortar and pestle and dry blended for 5 minutes with Avicel® RC591 and Sterotex K.
2. Powder blend transferred to a planetary mixer, and the EUDRAGIT™ NE40D dispersion was slowly added.
3. An additional aliquot of approximately 10% to 15% (based on dry weight of formulation) of distilled water was added to the powder/EUDRAGIT™ NE40D mass to achieve desirable wet massing.
4. Final wet mass allowed to mix for an additional 3–5 minutes.

II. Extrusion
Procedure
1. Extrusion of the wet mass in (I) was accomplished using a bench top extruder fitted with a 1.0 mm screen.
2. The rotation speed was set at maximum (approximately 25 rpm).
3. The extruded strands were collected periodically and processed further.

III. Spheronization
1. Spheronization was accomplished using a bench top spheronizer fitted with a fine cut plate.
2. An aliquot of approximately 100–150 gm of extruded material was charged into the chamber and spheronized as indicated below.
3. An air assist pressure of 0.2 Mpa was used to decrease the tackiness of the beads during spheronization.
4. The wet pellets were collected and gently screened through a 14 mesh screen to remove oversized particles. The oversized material was recycled into the extrusion mass to increase yield and decrease waste.

TABLE 32

Spheronization Time/Speed

| Time (min) | Percent of Maximum |
| --- | --- |
| 3–3.5 | 80% |
| Total Spheronization Time | 3–4 min |

IV. Collection and Sizing
Procedure
1. The wet pellets were collected and evenly spread onto aluminum sheets.
2. These sheets were then left at room temperature to dry overnight.
3. The dried pellets were collected, and the final bead distribution was assessed using standard metal screens and is shown below.
5. The percent of lost material in processing was less than 8%.
6. Pellets of the 16–20 mesh size were used in subsequent procedures.

TABLE 33

Pellet Size Distribution

| Pass Through (mesh) | Retained On (Mesh) | % of Starting Material |
| --- | --- | --- |
| 12 | 16 | 15.8 |
| 16 | 20 | 60.7 |
| 20 | Collection Plate | 15.6 |
| | Total | 92.1 |

V. Matrix Melting
Equipment
1. Melting of the wax matrix was accomplished with a fluidized bed coater fitted with an acrylic coating chamber and a filter screen.
2. The pellet cores were heated at 65° C. for 15 minutes and then allowed to cool at room temperature on aluminum sheets.

Figure 18:
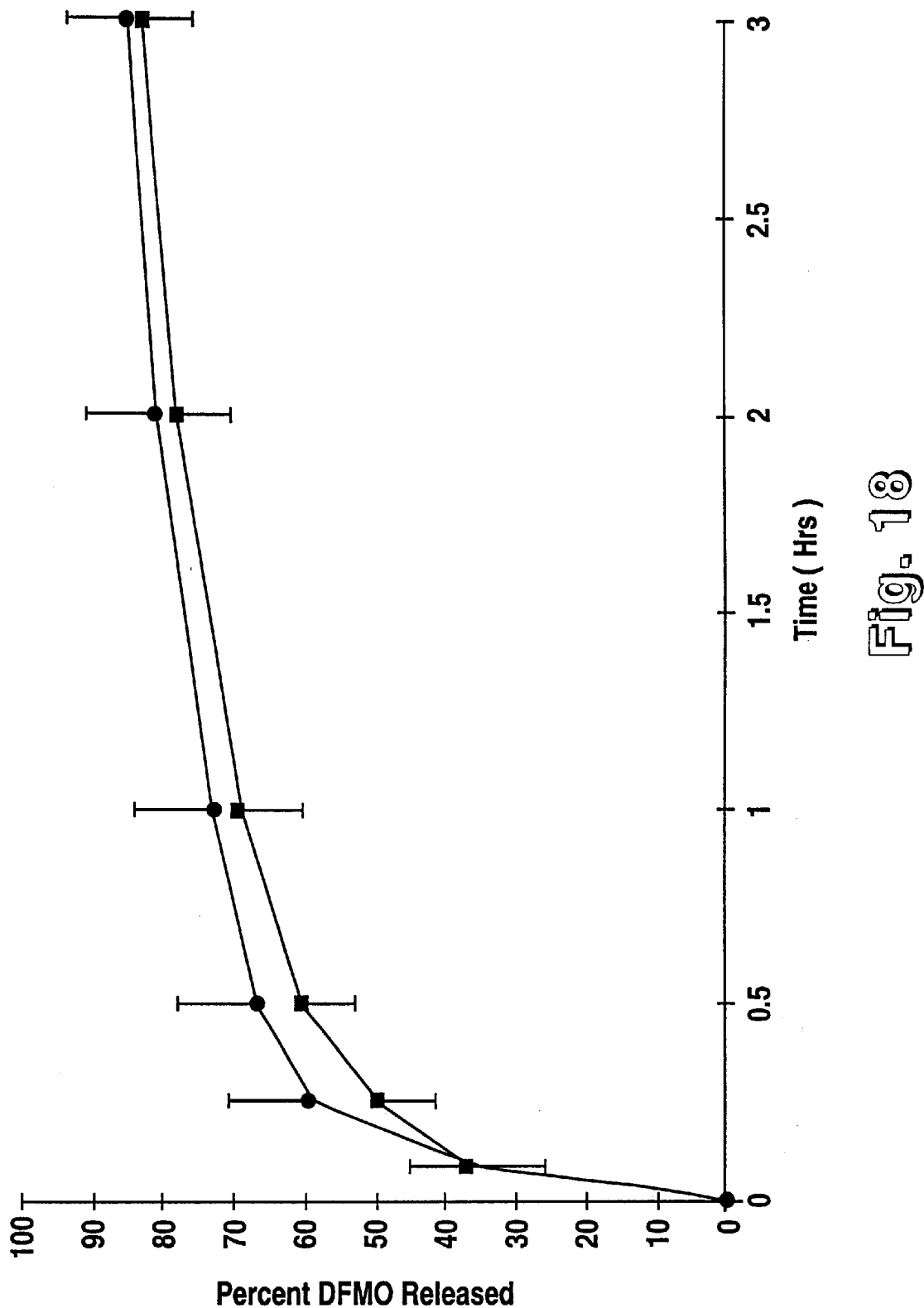
FIG. 18. Release profile in vitro of uncoated slow release matrix pellets at pH 7.4 (-■-) and pH of 1.0 (-●-). The data demonstrates that the release achieved with these pellets is pH independent.

The dissolution release profile of the uncoated slow-release DFMO-containing matrix pellets are illustrated at FIG. 18. In FIG. 18 (-●-●-●-) the dissoltion curve of DFMO from the matrix pellet is 0.1 N Hcl. The slight decrease in DFMO release in pH 7.4 is due to the relatively lower solubility of the drug DFMO at a neutral pH.

EXAMPLE 16

Release of DFMO from Coated Matrix Beads

The present example illustrates the use of the present invention with coated matrix beads containing DFMO. The release profiles here in an acidic media reflect poor adhesion of the EUDRAGIT™ L30D-55 and EUDRAGIT™ 4110D to the wax containing pellets containing DFMO. The rapid release of the drug was evident from both pellet formulations in the acidic medium as demonstrated in FIG. 19.

VI. Pellet Coating
Equipment
1. All coatings were applied with using a fluidized bed coater fitted with a Wurster insert and a bottom spray technique. A filter bag assembly was used, and the insert adjusted to ½" above the floor of the coating chamber in order to obtain a desirable flow of pellets through the spray path.
2. Coating material was supplied with a peristaltic pump, and the spray rate adjusted as indicated.
3. The atomization pressure was 1.0–1.2 bar, and the filter blow out pressure was set at 2 bar.
4. The coating charge was 300 gm of size 16–20 mesh pellets as described above except in the ethylcellulose/ 4110D coated product. The ethylcellulose/4110D coated product utilizes 300 gm of the rapid release beads detailed in the August 1997 report (lot #07219701).

Enteric Coating

TABLE 34

Coating Formulation

| Material | Based On | Weight |
| --- | --- | --- |
| EUDRAGIT ™ L30D-55 | | 88.9 gm |
| Triethyl Citrate (TEC) | 15%, dry weight polymer | 4.00 gm |

TABLE 34-continued

Coating Formulation

| Material | Based On | Weight |
|---|---|---|
| Imwitor ® 900 | 5%, dry weight polymer | 1.3 gm |
| Water | Total solids to be 15% | 92.5 gm |
| Total Suspension Weight | | 186.7 gm |

Calculation

For an 8.2% weight gain of polymer (x is dry weight of polymer) x/(300+x)=0.08 where x is 26.7 gm and is provided by 88.9 gm of 30% polymer suspension.

Procedure

1. The TEC, Imwitor® 90, and water are heated to approximately 65° C. and then homogenized at 4000 rpm for 15 minutes. The resultant dispersion is then allowed to cool to less than 30° C. before adding to the EUDRAGIT™ L30D-55.
2. The final coating dispersion is allowed to mix for at least 30 minutes prior to application.

TABLE 35

Spray Process

| Time (min) | Spray Rate (g/min) | Temperature (° C.) In/Out | Air Volume (M³/H) |
|---|---|---|---|
| 5 | 0 | 40/31 | 65 |
| 20 | 2.4 | 40/32 | 66 |
| 80 | 2.5 | 41/30 | 70 |

Beads were immediately coated with a 0.2% Imwitor® 900 top coat to prevent sticking during drying and storage.

0.2% GMS Top Coat

TABLE 36

Coating Formulation

| Material | Based On | Weight |
|---|---|---|
| Imwitor ® 900 | | 0.66 gm |
| Water | Total solids to be 2% | 32.54 gm |
| Total Suspension Weight | | 33.20 gm |

Calculation

For an 0.2% weight gain of polymer (x is dry weight of polymer) x/(332+x)=0.002 where x is 0.66 gm. Here, the coating charge is increased due to the weight gain of solid material from the previous spray applications.

Procedure

1. The Imwitor® 900 and water are heated to approximately 65° C. and then homogenized at 4000 rpm for 15 minutes.

TABLE 37

Spray Process

| Time (min) | Spray Rate (g/min) | Temperature (° C.) In/Out | Air Volume (M³/H) |
|---|---|---|---|
| 5 | 0 | 43/33 | 70 |
| 15 | 2.0 | 40/32 | 70 |
| 25 | 0 | 40/40 | 70 |

Curing

1. Coated beads were collected and spread evenly onto aluminum sheets.
2. Final product was cured at 40° C. for 2 hours and then at room temperature overnight Colonic Coating

TABLE 38

Coating Formulation

| Material | Based On | Weight |
|---|---|---|
| EUDRAGIT ™ 4110D | | 88.9 gm |
| Triethyl Citrate (TEC) | 5%, dry weight polymer | 1.3 gm |
| Imwitor ® 900 | 5%, dry weight polymer | 1.3 gm |
| Water | Total solids to be 15% | 95.2 gm |
| Total Suspension Weight | | 186.7 gm |

Calculation

For an 8.2% weight gain of polymer (x is dry weight of polymer) x/(300+x)=0.08 where x is 26.7 gm and is provided by 88.9 gm of 30% polymer suspension.

Procedure

1. The TEC, Imwitor® 900, and water are heated to approximately 65° C. and then homogenized at 4000 rpm for 15 minutes. The resultant dispersion is then allowed to cool to less than 30° C. before adding to the EUDRAGIT™ 4110D.
2. The final dispersion is allowed to mix for at least 30 minutes prior to application.

TABLE 39

Spray Process

| Time (min) | Spray Rate (g/min) | Temperature (° C.) In/Out | Air Volume (M³/H) |
|---|---|---|---|
| 5 | 0 | 35/33 | 70 |
| 15 | 2.0 | 36/29 | 70 |
| 65 | 2.5 | 37/26 | 70 |

Beads were immediately coated with a 0.2% Imwitor® 900 top coat to prevent sticking during drying and storage.

0.2% GMS Top Coat

TABLE 40

Coating Formulation

| Material | Based On | Weight |
|---|---|---|
| Imwitor ® 900 | | 0.66 gm |
| Water | Total solids to be 2% | 32.34 gm |
| Total Suspension Weight | | 33.00 gm |

Calculation

For an 0.2% weight gain of polymer (x is dry weight of polymer) x/(329+x)=0.02 where x is 0.66 gm. Here, the coating charge is increased due to the weight gain of solid material from the previous spray applications.

Procedure

1. The Imwitor® 900 and water are heated to approximately 65° C. and then homogenized at 4000 rpm for 15 minutes.

TABLE 41

Spray Process

| Time (min) | Spray Rate (g/min) | Temperature (° C.) In/Out | Air Volume (M³/H) |
|---|---|---|---|
| 5 | 0 | 43/33 | 70 |
| 15 | 2.0 | 40/32 | 70 |
| 25 | 0 | 40/40 | 70 |

Curing
1. Coated beads were collected and spread evenly onto aluminum sheets.
2. Final product was allowed to dry at room temperature overnight.

Figure 19:
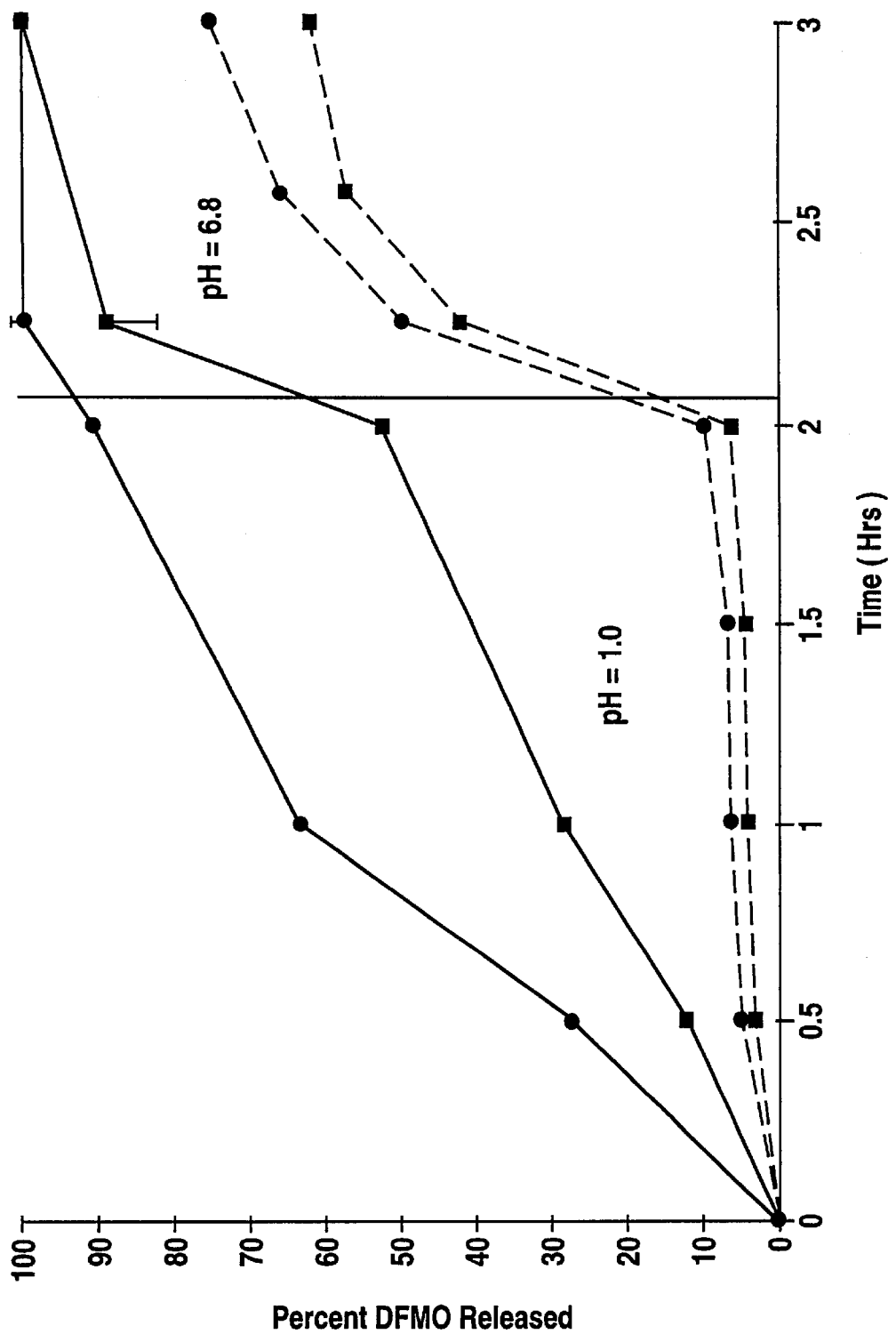
FIG. 19. Release of DFMO from coated wax containing matrix pellets at pH 1.0 and pH 6.8. (-■- -■- -■-)=EUDRAGIT™ 4110D coating; (-●-●-●-)= EUDRAGIT™ L30D-55). Proposed percent DFMO released from a preparation comprising a core of a wax matrix pellet having a first coat of Opadry® II (as a subcoat), and a second coat of a EUDRAGIT™ 4110D or S100, illustrated with dashed, filled squares (-■-■-■-). Proposed percent DFMO released from a preparation comprising a core of a wax matrix pellet with a first coat of Opadry® II (as a subcoat), and a second coat of EUDRAGIT™ L30D-55, is illustrated in the dashed, dotted line (●-●-●-●-●-●).

The poor adhesion of the EUDRAGIT™ used (L30D-55 and 4110D) to the wax containing pellet resulted in poor protection of the core when exposed to an acidic medium. When the pellets are coated with a 2% to 3% weight gain of Opadry® II prior to coating with the EUDRAGIT, protection of the pellets to the acidic medium will be provided. The EUDRAGIT™ polymers used here demonstrated enhanced adhesion to the Opadry® subcoat. The dissolution profiles of these pellet formulations represented by the two lower profiles in FIG. 19 provide the expected profile where a subcoat of Opadry® II is included.

EXAMPLE 17

Extended Release Coating

These pellets did not include a subcoating. They were coated with AQUA COAT® containing the Methacel, a coating of EUDRAGIT™ 4110D was then applied.

TABLE 42

Coating Formulation

| Material | Based On | Weight |
|---|---|---|
| AQUA-COAT ™ ® ECD | | 111.11 gm |
| Methocel ® K4M | | 3.33 gm |
| Triethyl Citrate (TEC) | 20%, dry weight polymer AQUA-COAT ™ ® ECD | 6.00 gm |
| Water | Total solids to be 10% w/w | 212.86 gm |
| Total Suspension Weight | | 333.30 gm |

(See FIG. 20 for data)

Calculation
For a 10% weight gain of polymer (x is dry weight of polymer) x/(300+x)=0.10 where x is 33.3 gm and is provided by 111.10 gm of 27% aqueous ethylcellulose polymer suspension and hydroxypropyl methylcellulose in a ratio of 9:1.

Procedure
1. The TEC and AQUA-COAT™ ® ECD were allowed to mix for at least thirty minutes before combining with the HPMC solution.
2. The HPMC was dispersed in hot water (1/3 of water for addition) and then diluted (2/3 of water for addition). The HPMC was allowed to hydrate and form a cool solution prior to addition to the AQUA-COAT™ ® ECD dispersion.
3. The final dispersion was stirred for at least 30 minutes prior to application.

TABLE 43

Spray Process

| Time (min) | Spray Rate (g/min) | Temperature (° C.) In/Out | Air Volume (M³/H) |
|---|---|---|---|
| 5 | 0 | 60/35 | 70 |
| 140 | 2.1–2.4 | 60/44 | 70 |
| 15 | 0 | 60/44 | 70 |

Curing
1. Coated beads were dried in situ for 15 minutes with the filter screen in place in preparation for the next application.

Colonic Coating of Extended Release Pellets

TABLE 44

Coating Formulation

| Material | Based On | Weight |
|---|---|---|
| EUDRAGIT ™ 4110D | | 90.49 gm |
| Triethyl Citrate (TEC) | 5%, dry weight polymer | 1.36 gm |
| Imiwitor ® 900 | 5%, dry weight polymer | 1.36 gm |
| Water | Total solids to be 15% | 98.80 gm |
| Total Suspension Weight | | 191.01 gm |

Calculation
For an 7.4% weight gain of polymer (x is dry weight of polymer) x/(339+x)=0.074 where x is 27.15 gm and is provided by 90.49 gm of 30% polymer suspension. Here, the coating charge is increased due to the weight gain of solid material from the previous spray application.

Procedure
1. The TEC, Imwitor® 900, and water are heated to approximately 65° C. and then homogenized at 4000 rpm for 15 minutes. The resultant dispersion is then allowed to cool to less than 30° C. before adding to the EUDRAGIT™ 4110D dispersion.
2. The final dispersion is allowed to stir for at least 30 minutes prior to application.

TABLE 45

Spray Process

| Time (min) | Spray Rate (g/min) | Temperature (° C.) In/Out | Air Volume (M³/H) |
|---|---|---|---|
| 5 | 0 | 50/41 | 70 |
| 63 | 2.1–2.5 | 39/29 | 70 |

Beads were immediately coated with a 0.2% Imwitor® 900 top coat to prevent sticking during drying and storage.
0.2% GMS Top Coat

TABLE 46

Coating Formulation

| Material | Based On | Weight |
|---|---|---|
| Imwitor ® 900 | | 0.74 gm |
| Water | Total solids to be 2% | 36.16 gm |
| Total Suspension Weight | | 36.84 gm |

Calculation
For an 0.2% weight gain of polymer (x is dry weight of polymer) x/(369+x)=0.002 where x is 0.74 gm. Here, the coating charge is increased due to the weight gain of solid material from the previous spray applications.

Procedure

1. The Imwitor® 900 and water are heated to approximately 65° C. and then homogenized at 4000 rpm for 15 minutes.

TABLE 47

Spray Process

| Time (min) | Spray Rate (g/min) | Temperature (° C.) In/Out | Air Volume (M³/H) |
|---|---|---|---|
| 3 | 0 | 39/33 | 70 |
| 15 | 2.1–2.5 | 39/30 | 70 |
| 10 | 0 | 40/40 | 70 |

Curing

1. Coated beads were collected and spread evenly onto aluminum sheets.
2. Final product dried at 40° C. overnight.

VI. Dissolution Testing

Apparatus

1. Testing was done using the USP Method I, rotating basket procedure.
2. All testing was done at 37° C. and 100 rpm shaft speed.
3. Various dissolution media was used to approximate the in vivo conditions that the pellets may experience.
4. Three milliliter samples were drawn at set time points, and blank dissolution media was added to maintain a constant dissolution volume
5. Final dissolution volumes were 500 ml.
6. Initial media was 0.1 N HCL and, if needed, aliquots of 0.2 M sodium phosphate tribasic was added to increase the pH. At pH changes after the addition of the 0.2 M sodium phosphate, the pH of the individual kettles was adjusted with 2 N NaOH prior to sampling.
7. Dissolution samples were filtered with a 0.45 $\mu$m PTFE filter prior to analysis.

TABLE 48

Dissolution Time and Media

| Product | Time | Media | pH |
|---|---|---|---|
| Uncoated Pellets | 0–180 min | 0.1N HCl | 1.0 |
| | | 0.05M Phosphate 500 ml | 7.4 |
| EUDRAGIT ™ L30D-55 | 0–120 min | 0.1N HCl 375 ml | 1.0 |
| | 120–240 min | +125 ml 0.2M NaPO₄ | 6.8 |
| EUDRAGIT ™ 4110D | 0–120 min | 0.1N HCl 375 ml | 1.0 |
| | 120–240 min | +125 ml 0.2M NaPO₄ | 6.8 |
| AQUA-COAT ™ ® ECD + EUDRAGIT ™ 4110D | 0–120 min | 0.1N HCl 375 ml | 1.0 |
| | 120–240 min | +125 ml 0.2M NaPO₄ | 6.8 |
| | 240–480 min | Adjust to pH | 7.4 |

As demonstrated in FIG. 20, retardation of drug release in an acidic (0.1 N HCl) was attained at pH 6.8, the EURDRAGIT™ 4110D dissolved and during the next 2 hours, the drug diffused through the pores in the AQUA-COAT™ film.

VII. Drug Content

Procedure

1. An aliquot of pellets was ground with a porcelain mortar and pestle.
2. Approximately 500 mg aliquot of the ground material was transferred to a 250 ml volumetric flask and brought to 3/4 volume with 0.1 N HCl.
3. The flasks were then sonicated for 20 minutes and allowed to cool to room temperature before bringing up to volume with distilled water.
4. Sample aliquots were filtered with a 0.45 $\mu$m filter prior to analysis.

VIII. Drug Analysis

| HPLC Conditions | |
|---|---|
| Column: | Alltech Platinum EPS ™ C18, ODS-1,5 $\mu$m |
| Mobile Phase: | 1.1 mM Sodium Dodecyl Sulfate in 20/80 v/v Acetonitrotrile/0.05M NaPO₄ (pH = 2.3) |
| Flow Rate: | 1.0 ml/min |
| Detection: | 210 nm |
| Injection Volume: | 50 $\mu$l |
| Retention Time: | 4.2 minutes |

EXAMPLE 18

Multi-Layered Matrix Tablet

The present example is provided to demonstrate the utility of the present invention as a multi-layered tablet that includes a core of a matrix containing DFMO, and a slow release material. Such slow release materials include by way of example, Klucel™, HPMC, carbomer, Polyox, and other cellulosic and hydrophilic polymers, proteins and polysaccharides.

In some embodiments, the tablet will include a core pellet of DFMO in a matrix. An exemplary matrix retardant used in the present example is Klucel. This core tablet will then have a first coat of a colonic protective material, such as EUDRAGIT™ S100. This first coat is then covered with an Opadry® solution of HPMC or similar rapidly dissolving or freely permeable material, also containing DFMO (2nd coat). Over this, a third coat of an acid resistant polymer (e.g. EUDRAGIT™ L, CAP, CAT, PVAP, HPMCP, HPMCAS, or similar enteric polymer is applied over the second coat. Then, a fourth coat of an immediate release material (e.g. Opadry®) containing DFMO is applied.

The matrix tablet may be prepared by blending the DFMO (45%) with Klucel HF (25%), spray dried lactose (24%) and Starch 1500 (5%) in a suitable blender for 10 minutes. The magnesium stearate (0.5%) and Cabosil M5P (0.5%) are added to the powders. This is blended for an additional 5 minutes. The powder blend is then compressed into tablets in the 8–10 kg range in the 200–400 mg range. The tablets are then coated as described above.

| Exemplary Weight Gain for Pellet Coatings | | |
|---|---|---|
| Coat 1 | EUDRAGIT ™ S100 | 8% weight gain |
| Coat 3 | L30 D-55 | 8% weight gain |
| Coat 2, Coat 4 | HPMC E5:DFMO (ratio 5:1) | 10% weight gain |

Other chemical synthetic techniques well known to those of skill in the art may be used such as that described in the attached list of references which are hereby incorporated in their entirety.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

Those of skill in the art should, in light of the present disclosure, appreciate that many changes can be made in the specific embodiments where are disclosed herein and still obtain a like or similar result without departing from the spirit and scope of the invention. All of the compositions and methods disclosed and claimed herein can be made and executed without undue experimentation in light of the present disclosure. It will be apparent that certain compounds which are both physiologically and chemically related may be substituted for the therapeutic compound described herein while the same or similar results are achieved.

REFERENCES

The following references, to the extent that they provide exemplary procedural or other details supplementary to those set forth herein, are specifically incorporated herein by reference.

S. G. Eckhardt, D. Dai, K. K. Davidson, B. J. Forseth, G. M. Wahl, D. D. Von Hoff, Proc. Nat'l. Acad. Sci., USA, 1994, 91, 6674–6679.

Controlled Drug Delivery: Fundamentals and Applications, 2nd ed. (Joseph R. Robinson and Vincent H. L. Lee, eds., Marcel Dekker, Inc., NY; 1987) ISBN 0-8247-7588-0

Aqueous Polymeric Coatings for Pharmaceutical Dosage Forms (James W. McGinity, ed.; Marcel Dekker, Inc., NY; 1989) ISBN 0-8247-7907-X Pharmaceutical Dosage Forms: Tablets Vol. 3 (Herbert A. Lieberman, Leon Lachman and Joseph B. Schwartz, eds.; Marcel Dekker, Inc., NY; 1990) ISBN 0-8247-8300-X Pharmaceutical Dosage Forms and Drug Delivery Systems, 6th Ed. (Howard C. Ansel, Nicholas G. Popovich and Lloyd V. Allen, Jr., eds.; Williams & Wilkins, Baltimore; 1995) ISBN 0-683-00193-0

Development of Difluoromethylornithine as a Chemoprevention Agent for the Management of Colon Cancer, Meyskens, Frank L., Jr.; Gerner, Eugene W. J., J. Cell Biochem. (1995) (Suppl. 22), 126–31

Dose De-Escalation Chemoprevention Trial of Alpha-Difluoromethylornithine in Patients with Colon Polyps. (Meyakens, F. L., Jr; Emerson, S. S.; Pelot, D.; Meshkinpour, H.; Shassetz, L. R.; Einspahr J.; Alberts, D. S.; Gerner, E. W. Aug. 3, 1994 ) Journal of the National Cancer Institute, (Aug. 3, 1994) 86 (15) 1122–30.

Cancer Chemoprevention. (Lippman S. M.; Benner S. E.; Waun Ki Hong J. Clin. Oncol., (1994) 12/4 (851–873).

Alpha-Difluoromethylornithine (DFMO) as a Potential Chemopreventive Agent: Toxicology, Pharmacokinetics and Pharmacodynamics of Chronic Oral Administration in Humans (Meeting abstract); Creaven, P. J.; Pendyala, L.; Porter, C. W.; Murphy, M. J. Non-serial, (1993). CCPC-93: Second International Cancer Chemo Prevention Conference. Apr. 28–30, 1993, Berlin, Germany, p. 53.

Randomized Phase I Chemoprevention Dose-Seeking Study of Alpha-Difluoromethylornithine; Love, R. R.; Carbone, P. P.; Verma, A. K.; Gilmore, D.; Carey, P.; Tutsch, K. D.; Pomplun, M.; Wilding, G., Journal of the National Cancer Institute, (May 5, 1993), 85 (9) 732–7.

Urinary and Erythrocyte Polyamines During the Evaluation of Oral Alpha-Difluoromethylornithine in a Phase I Chemoprevention Clinical Trial; Pendyala, L.; Creaven, P. J.; Porter, C. W., CANCER EPIDEMIOLOGY, BIOMARKERS AND PREVENTION, (May-June 1993) pg. 235–41.

Polyamine Depletion as a Strategy for Cancer Chemoprevention: Rationale, Problems and Solutions (Meeting Abstract). (Gerner, E. W. Non-serial, Jun. 3–6, 1992, Tucson, Ariz.). Fourth International Conference on Prevention of Human Cancer: Nutrition and Chemoprevention Controversies.

PHASE I STUDY OF DIFLUOROMETHYLORNITHINE DFMO AS A CHEMOPREVENTIVE AGENT (CPA) (MEETING ABSTRACT); Creaven, P. J.; Pendyala, L.; Petrelli, N.; Douglass, H.; Herrera, L.; Porter, C.; Solomon, J.; Proc. Annul Meet. Am. Soc. Clin. Oncol. (1992) Vol. 11, pp. A395.

Polyamine Contents in Rectal and Buccal Mucosae in Humans Treated With Oral Difluoromethylornithine; Boyle, J. O.;Meyakens, .F L., Jr.; Garewal, H. S.; Gerner, E. W.; Cancer Epidemiology Biomarkers & Prevention (1992) 1 (2). pg. 131–135.

Chemoprevention Trials (Meeting Abstract); Kelloff, G. J.; Malone, W. F.; Steele, V.; Boone, C. W.; Third International Conference on Mechanisms of Antimutagenesis and Anticarcinogenesis. (May 5–10, 1991) Lucca, Italy, p. 42.

DIFLUOROMETHYLORNITHINE (DFMO), A POTENTIAL CHEMOPREVENTIVE (MEETING ABSTRACT); Carbone, P. P.; Love, R. R.; Carey, P.; Tutsch, K.; Verma, A. K.; Wilding, G.; Gilmore-Cunningham, D., Proc. Annul Meet. Am. Assoc. Cancer Res., (1991) Vol. 32, pp. A1209.

Phase I Trial and Pharmacokinetic Study of Intravenous and Oral Alpha-Difluoromethylornithine; Griffin C. A.; Slavik, M.; Chien, S. C.; Hermann, J.; Thompson, G.; Blanc, O.; Invest. New Drugs (1987) 5, No. 2, 177–86.

Phase II Trials of Alpha-Difluoromethylornithine, an Inhibitor of Polyamine Synthesis, in Advanced Small Cell Lung Cancer and Colon Cancer, Abeloff, M. D.; Rosen, S. T.; Luk, G. D.; Baylin, S. B.; Zeltzman, M.; Sjoerdsma, A. Cancer Treatment Reports, (1986) 70 (7) 843–5.

Phase I Trial and Pharmacokinetic Studies of Alpha Difluoromethylornithine an Inhibitor of Poly Amine Biosynthesis; Abeloff, M. D.; Slavik, M.; Luk, G. D.; Griffin, C. A.; Hermann, J.; Blanc, O.; Sjoerdsma, A.; Baylin, S. B.; J. Clin. Oncol. (1984)2 (2). pg. 124–130.

Regional Chemoprevention of Carcinogen-Induced Tumors in Rat Colon; Liu, T.; Mokuolu, A. O.; Rao, C. V.; Reddy, B. S.; Holt, P. R.; Gastroenterology, (1995) pg. 109/4 (1167–1172).

Placebo-Controlled Randomized Trial of DFMO As A Chemopreventive Agent in Patients at High Risk For Colorectal Cancer, Jacoby, R. F.; Verma, A. K.; Tutsch, K. D.; Mamby, C. A.; Love, R. R.; Dept of Medicine, University of Wisconsin, Madison, Wis., U.S.A; J.Invest Med. (1995) (43, Suppl. 2,411A.)

Development of Difluoromethylornithine as a Chemoprevention Agent for the Management of Colon Cancer. (Meyskens, F. L.; Gerner, E. W.; Department of Medicine and Clinical Cancer Center, University of California, Irvine, 101 City Drive South, Building 23, Route 81, Orange, Calif. 92668, U.S.A. J. Cell. Biochem. (1995) (Suppl. 22, 126–31,) 3 FIG. 2 Tab. 12 Ref.

Placebo-Controlled Randomized Trial of DFMO As A Chemopreventive Agent in Patients at High Risk for Colorectal Cancer; Jacoby, R. F.; Verma, A. K.; Tutsch, K. D.; Mamby, C. A.; Love, R. R. Madison, Wis., U.S.A.; Gastroenterology (108, No. 4, Suppl., A485,)

Chronic Toxicity Studies of the Potential Cancer Preventive 2-(difluoromethyl)-d,1-ornithine. (Crowell, J. A.; Goldenthal, E. I.; Kelloff, G. J.; Malone, W. F.; Boone, C. W. FUNDAM. APPL. TOXICOL., (1994) 22i3 (341–354).

Oral Precancer: Preventive and Medical Approaches to Management; Scully, C., London, U. K.; Bur. J. Cancer Oral Oncol. (1995) (31, No. 1, pg. 16–26, 1

Chemopreventive Drug Development: Perspectives and Progress. Kelloff, G. J.; Boone, C. W.; Crowell, J. A.; Steele, V. E.; Lubet R.; Sigman C. C. Bethesda, M D. CIDU, National Cancer Institute, (1994) (85–98).

Chemoprevention of Barrett's Esophagus and Oral Leukoplakia Garewal, H S; University of Arizona Cancer Center, Tucson. Adv Exp Med Biol, (1992) pg. 320 129–36.

Polyamines as Biomarkers of Cervical Intraepithelial Neoplasia Nishioka, Kenji; Melgarejo, Alejandro B.; Lyon, Rosanna R.; Mitchell, Michele Follen, Dep. of Surgical Oncology, Univ. of Tex., Houston, Tex., TX, 77030. J. Cell. Biochem. (1995), (Suppl. 23), (1995) pg. 87–95

Chemoprevention Trials and Surrogate End Point Biomarkers in the Cervix; Mitchell, Michele Follen; Hittelman, Walter K.; Lotan, Reuben; Nishioka, Kenji; Tortolero-Luna, Guillermo; Richards-Kortum, Rebecca; Wharton, J. Taylor, Hong, Waun K. 1995 Houston, Tex.) M. D. Anderson Cancer Center, University Texas, Cancer (Philadelphia), (1995) pg. 76(10, Suppl., American Cancer Society Low Dose Difluoromethylornithine (DFMO) Produces Significant Changes in Polyamine Content of Upper GI Mucosa in Patients with Barrett's Esophagus; Garewal, H S; Sampliner, R E; Fennerty, M B; Gerner, E., Tucson, Ariz.) Gastroenterology (100, No. 5,Pt. 2,A364), (1991) 1 Ref.

Cancer Prevention Research Trials; Greenwald, P.; Malone, W. F.; Cerny, M. E.; Stem, H. R., Maryland 20892, U.S.A. 1993). Adv.Cancer Res. (1993) (61, 1–23, 1993) 5 FIG. 4 Tab. 74 Ref Tumor Necrosis Factor-Induced Cytotoxicity is Accompanied by Intracellular Mitogenic Signals in ME-180 Human Cervical Carcinoma Cells; Manchester, K. M.; Heston, W. D.; Donner, D. B.). Laboratory of Peptide Hormone Action, Memorial, New York, N. Y. 10021.

Chemoprevention of Colon Carcinogenesis by Dietary Administration of Piroxicam, .Alpha.-Difluoromethyl ornithine, 16.alpha.-Fluoro-5-androsten-17-one, and Ellagic Acid Individually and in Combination; Rao, Chinthalapally V.; Tokumo, Kenji; Rigotty, Jeff; Zang, Edith; Kelloff, Gary; Reddy, Bandaru S.; Div. Nutr. Carcinog., American Health Found., Valhalla, N.Y., 10595, USA Cancer Res. (1991), 51 (17), 4528–34

Griffin C., Abeloff M D, Slavik M., et al. Phase I trial and pharmacokinetic study of intravenous and high dose oral α-difluoromethylornithine (DFMO). Proc ASCO 3:34, 1984.

Goldenthal, E. I. (1990). One Year Oral Toxicity Study of Difluoromethylornithine in Rats and in Dogs. International Research and Development Corporation, Reports 560–032 and 560–033.

Loprinzi, C. L., Love, R. R. Therneau, T. M., and Verma, A. K.; Inhibition of human skin ornithine decarboxylase activity by oral difluoromethylornithine. *Cancer Ther. Control* 1, (1989) 75–80.

Luk, G. D.; Clinical and biologic studies of DFMO in the colon. In *Cancer Chemoprevention* (L. Wattenberg, M. Lipkin, C. W. Boone, and G. J. Kelloff, Eds.), (1992) pp. 515–530. CRC Press, Boca Raton, Fla.

Creaven P J, Pendyala L., Petreli N J: Evaluation of a α-difluoromethylornithine as a potential chemoprevention agent: Tolerance to daily oral administration in humans. Cancer Epidemiol Biomarkers Prev 2:243–247, (1993).

Croghan M K, Aickin M G, Meyakens F L Jr: Dose-related α-difluoromethylornithine ototoxicity. Am J Clin Oncol 14:331–335, (1991).

A Delayed Delivery System for the Colonic Drug Release; M. A. Vandelli et al., Proc. 1st World Mtg. APGI/APV, Budapest, 9/11, May 1995, pg. 278–279.

The Relation Between Swelling Properties and Enzymatic Degradation of Azo Polymers Designed for Colon-Specific Drug Delivery; G. Van den mooter et al., Pharmaceutical Res. (1994), 11 (12), pg. 1737–1741.

Characterization of Colon-Specific Azopolymers: A Study of the Swelling Properties and the Permeability of Isolated Polymer Fiulms; G. Van den mooter et al., Internat'l. J. Pharmaceutics (1994), 111 pg. 127–136.

Enteric Coated Timed Release Systems for Colonic Targeting; I. R. Wilding et al.; Internat'l . J. Pharmaceutics (1994), 111 ,pg. 99–102.

In Vivo Evaluation of a Colon-Specific Drug Delivery system: An Absorption Study of Theophylline from Capsules Coated with Azo Polymers in Rats; Pharmaceutical Res. (1995), 12(2), pg. 244–247.

Colonic Drug Delivery; T. N. Toer, Proceed. Intern Symp. Control Rel. Bioact. Mater., Mar. 16 (1990), pg. 126–127, pg. 291–295.

In Vitro and In Vivo Analysis of Colon Specificity of Calcium Pectinate Formulations; A. Rubinstein et al., Eur. J. Pharm. Biopharm. (1995), 41(5), pg. 291–295.

What is claimed is:

1. A pharmaceutical formulation comprising:

(a) a core having a rapid release DFMO-containing granule and a slow release DFMO-containing granule, said granules comprising (+)-DFMO, (−)-DFMO or a defined ratio of (+)-DFMO:(−)-DFMO, or pharmaceutically acceptable salts thereof; and (b) an outer layer surrounding said core comprising a pH-responsive coating, wherein the rapid release granule releases DFMO within two hours after dissolution of the outer layer, and the slow release granule releases DFMO within eight hours after dissolution of the outer layer.

2. The pharmaceutical formulation of claim 1, wherein the pH-responsive coating is further defined as providing for release of DFMO at a pH of about 6.0.

3. The pharmaceutical formulation of claim 1, wherein the DFMO-containing granules are further defined as comprising:

(a) a granule wherein at least a portion of the drug is released in the gastric region;

b) a granule wherein at least a portion of the drug is released in the enteric region; and (c) a granule wherein at least a potion of the drug is released in the colorectal region, wherein each granule comprises (+)-DFMO, (−)-DFMO or a defined ratio of (+)-DFMO:(−)-DFMO, or pharmaceutically acceptable salts thereof.

4. The pharmaceutical formulation of claim 1, wherein the formulation provides a detectable plasma concentration of DFMO in the range of about 0.1 $\mu$M to about 1000 $\mu$M.

5. The pharmaceutical formulation of claim 4, wherein the formulation provides a detectable plasma concentration of DFMO in the range of about 1 $\mu$M to about 100 $\mu$M.

6. A multi-coated pharmaceutical formulation comprising:
   (a) a core pellet of DFMO-containing granules in a slow-release matrix;
   (b) a first coat of a colonic protective material;
   (c) a second coat comprising a pore forming agent;
   (d) a rapidly dissolving polymeric material and DFMO;
   (e) a third coat comprising an acid resistant polymer; and
   (f) a fourth coat comprising a pore-forming agent and DFMO.

7. The multi-coated pharmaceutical formulation of claim 6, wherein the DFMO-containing granules comprise coated DFMO-containing granules and uncoated DFMO-containing granules.

* * * * *